US008426364B2

(12) United States Patent  (10) Patent No.: US 8,426,364 B2
Mochly-Rosen et al.  (45) Date of Patent: Apr. 23, 2013

(54) METHOD OF PREVENTING PROGRESSION OF HYPERTENSION-INDUCED HEART FAILURE WITH PKC PEPTIDES

(75) Inventors: Daria D. Mochly-Rosen, Menlo Park, CA (US); Koichi K. Inagaki, Shiga (JP)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 178 days.

(21) Appl. No.: 12/774,669

(22) Filed: May 5, 2010

(65) Prior Publication Data

US 2010/0286050 A1  Nov. 11, 2010

Related U.S. Application Data

(62) Division of application No. 11/809,521, filed on Jun. 1, 2007, now Pat. No. 7,741, 290.

(60) Provisional application No. 60/810,760, filed on Jun. 6, 11.

(51) Int. Cl.
*A61K 38/08* (2006.01)
*C07K 7/06* (2006.01)

(52) U.S. Cl.
USPC .......... 514/16.4; 514/21.8; 530/800; 530/329

(58) Field of Classification Search .................. 514/16.4, 514/21.8; 530/800, 329
See application file for complete search history.

(56) References Cited

U.S. PATENT DOCUMENTS

| 5,723,456 | A * | 3/1998 | Jirousek et al. ............... 514/183 |
| 5,783,405 | A | 7/1998 | Mochly-Rosen et al. |
| 6,165,977 | A | 12/2000 | Mochly-Rosen |
| 6,225,301 | B1 | 5/2001 | Ways et al. |
| 6,933,275 | B2 | 8/2005 | Mochly-Rosen et al. |
| 2002/0168354 | A1 | 11/2002 | Mochly-Rosen |
| 2003/0055097 | A1 | 3/2003 | Zhang et al. |
| 2003/0134774 | A1 | 7/2003 | Steinberg et al. |
| 2004/0009922 | A1 * | 1/2004 | Mochly-Rosen ............... 514/16 |
| 2004/0186055 | A1 | 9/2004 | Mochly-Rosen |
| 2005/0164947 | A1 | 7/2005 | Mochly-Rosen et al. |
| 2006/0148700 | A1 | 7/2006 | Mochly-Rosen et al. |
| 2006/0148702 | A1 | 7/2006 | Mochly-Rosen et al. |
| 2007/0066526 | A1 | 3/2007 | Mochly-Rosen et al. |

FOREIGN PATENT DOCUMENTS

WO  WO 2005/082367 A1  9/2005

OTHER PUBLICATIONS

Kim-Mitsuyama et al., "Additive beneficial effects of the combination of a calcium channel blocker and an angiotensin blocker on a hypertensive rat-heart failure model," Hypertens Res 27(10):771-779, 2004.*

(Continued)

*Primary Examiner* — Rosanne Kosson
(74) *Attorney, Agent, or Firm* — Judy Mohr; McDermott Will & Emery LLP

(57) ABSTRACT

Methods are described for slowing or inhibiting the progression of heart failure in a mammalian subject suffering from chronic hypertension. The methods involve administering an εPKC, βIPKC, or βIIPKC peptide inhibitor, examples of which are provided.

7 Claims, 18 Drawing Sheets

OTHER PUBLICATIONS

Chen, et al., "Cardioprotection from ischemia by a brief exposure to physiological levels of ethanol: role of epsilon protein kinase C", PNAS, vol. 96, No. 22, pp. 12784-12789 (1999).

Chen, et al., "Molecular transporters for peptides: Delivery of a cardioprotective εPKC agonist peptide into cells and intact ischemic heart using a transport system, $R_7$", Chem. Biol., vol. 140, pp. 1-7 (2001).

Dorn, et al., "Sustained in vivo cardiac protection by a rationally designed peptide that causes epsilon protein kinase C translocation", PNAS, vol. 96, No. 22, pp. 12798-12803 (1999).

Iemitsu, et al., "Cardiac hypertrophy by hypertension and exercise training exhibits different gene expression of enzymes in energy metabolism", Hypertension Res., vol. 26, No. 1, pp. 829-837 (2003).

Inagaki, et al., "Inhibition of delta-protein kinase C protects against reperfusion injury of the ischemic heart in vivo", Circulation, vol. 108, pp. 2304-2307 (2003).

Inagaki, et al., "Pharmacological inhibition of epsilon PKC prevents the progression of hypertension-Induced heart failure", Circulation, vol. 114, No. 18, p. 442 (2006) *Abstract Only*.

International Search Report from related PCT Patent Application No. PCT/US2007/012985 mailed on Jan. 2, 2008, application published as WO 2007/143119 A3 on Dec. 12, 2007.

Kubo, et al., "Primary structures of human protein kinase C beta I and beta II differ only in their C-terminal sequences", FEBS Lett., vol. 223, No. 1, 138-142 (1987).

\* cited by examiner

SEQUENCE LISTING

<160> NUMBER OF SEQ ID NOS: 7

<210> SEQ ID NO 1
<211> LENGTH: 11
<212> TYPE: PRT
<213> ORGANISM: Artificial Sequence
<220> FEATURE:
<223> OTHER INFORMATION: Synthetic TAT peptide

<400> SEQUENCE: 1

Tyr Gly Arg Lys Lys Arg Arg Gln Arg Arg Arg
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic PKC peptide inhibitor

<400> SEQUENCE: 2

Lys Leu Phe Ile Met Asn
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide inhibitor

<400> SEQUENCE: 3

Gln Glu Val Ile Arg Asn
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide inhibitor

<400> SEQUENCE: 4

Ser Phe Asn Ser Tyr Glu Leu Gly Ser Leu
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic PKC peptide inhibitor

<400> SEQUENCE: 5

Glu Ala Val Ser Leu Lys Pro Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

His Asp Ala Pro Ile Gly Tyr Asp

```
<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Arg Gln Ile Lys Ile Trp Phe Gln Asn Arg Arg Met Lys Trp Lys Lys
1               5                   10                  15
```

METHOD OF PREVENTING PROGRESSION OF HYPERTENSION-INDUCED HEART FAILURE WITH PKC PEPTIDES

CROSS REFERENCE TO RELATED APPLICATIONS

The application is a Divisional application of U.S. patent application Ser. No. 11/809,521, filed Jun. 1, 2007, now U.S. Pat. No. 7,741,290, issued on Jun. 22, 2010, which claims the benefit of U.S. Provisional Application No. 60/810,760, filed Jun. 1, 2006, each of which is incorporated herein by reference in its entirety.

STATEMENT REGARDING FEDERALLY SPONSORED RESEARCH

This invention was made with the support of National Institute of Health Grant number HL-076675. Accordingly the United States government has certain rights in this invention.

REFERENCE TO SEQUENCE LISTING, TABLE OR COMPUTER PROGRAM

A "Sequence Listing" is submitted with this application in the form of a text file, created 29 Apr. 2010 and modified 7 Jun. 2010, named "586008239US01seqlist.txt" (4096 bytes on disk), the content of which are incorporated herein by reference in their entirety.

TECHNICAL FIELD

The subject matter described herein relates to peptides for inhibiting the progression of heart disease by inhibiting isozymes of protein kinase C.

BACKGROUND

Heart failure is a growing public health problem in the United States. Currently, five million people suffer from heart failure (1) and despite considerable advances in pharmacological therapy, device technology and heart transplantation, mortality associated with heart failure increased by twenty percent from 1993 to 2003. Nearly one in three adults has hypertension in the United States (47). Seventy four percent who have congestive heart failure have blood pressure higher than 140/90 mmHg (1). The cause of heart failure is predominantly ischemic disease in non African-Americans but is related primarily to hypertension in African-Americans (48). Thus, hypertensive heart failure is still a clinical problem despite advances in anti-hypertensive agents.

Angiotensin I converting enzyme inhibitors and angiotensin II type 1 receptor blockers (ARB) are the clinical treatments for patients with heart failure (2). Because many of the signaling events associated with heart failure, including the rennin-angiotensin system, involve activation of protein kinase C (PKC) (3-5), it is of interest to determine whether PKC should be targeted for the development of new therapeutics.

The isozyme $\epsilon$PKC is of particular interest. Several studies report that the level and activity of $\epsilon$PKC increase in cardiac hypertrophy (3, 6). In transgenic mice, overexpression of the active form of $\epsilon$PKC induces eccentric hypertrophy and reduces cardiac functions, leading to heart failure (7, 8). In contrast, selective expression of an $\epsilon$PKC-activating peptide in cardiac myocytes induces concentric hypertrophy with improved cardiac function, while expression of an $\epsilon$PKC-inhibiting fragment results in eccentric hypertrophy and heart failure in a gene dose-dependent manner (9, 10). Finally, mice lacking $\epsilon$PKC have normal cardiac function (11). Thus, conflicting data on the role of $\epsilon$PKC in heart failure have been obtained using genetically manipulated mice and the possible effect of $\epsilon$PKC during heart development further complicates their interpretation. Selective pharmacological agents that regulate $\epsilon$PKC during the transition to heart failure may be better suited to determine the role of $\epsilon$PKC in heart failure.

Isozyme-selective $\epsilon$PKC inhibiting and activating peptides have been previously described (12). These regulators were developed based on the observation that the interaction of each PKC isozyme with its anchoring protein, the receptor for activated C-kinase (RACK), is required for its functions upon activation (13). The $\epsilon$PKC isozyme inhibiting peptide, $\epsilon$V1-2, corresponds to a sequence in the RACK-binding site on this isozyme, and the selective $\epsilon$PKC isozyme activating peptide, $\Psi\epsilon$RACK, is derived from a sequence in $\epsilon$PKC that shares homology with its RACK (9, 12). These peptides are linked to membrane permeable peptides, $TAT_{47-57}$, to enable their effective intracellular delivery (14, 15) and are therefore useful pharmacological tools.

Strategies and treatment methods to alter the progress of heart failure are desired in the art.

The foregoing examples of the related art and limitations related therewith are intended to be illustrative and not exclusive. Other limitations of the related art will become apparent to those of skill in the art upon a reading of the specification and a study of the drawings.

REFERENCES

The following references and other references cited herein are hereby incorporated by reference in their entirety.

1. Thom, T. et al. (2006) Heart disease and stroke statistics—2006 update: a report from the American Heart Association Statistics Committee and Stroke Statistics Subcommittee. *Circulation* 113:e85-151.
2. Cohn, J. N. and Tognoni, G. 2001. A randomized trial of the angiotensin-receptor blocker valsartan in chronic heart failure. *N Engl J Med* 345:1667-1675.
3. Inagaki, K. et al. (2002) Tissue angiotensin II during progression or ventricular hypertrophy to heart failure in hypertensive rats; differential effects on PKC epsilon and PKC beta. *J Mol Cell Cardiol* 34:1377-1385.
4. Takeishi, Y. et al. (1999) Responses of cardiac protein kinase C isoforms to distinct pathological stimuli are differentially regulated. *Circ Res* 85:264-271.
5. Sabri, A. and Steinberg, S. F. (2003) Protein kinase C isoform-selective signals that lead to cardiac hypertrophy and the progression of heart failure. *Mol Cell Biochem* 251:97-101.
6. Gu, X. and Bishop, S. P. (1994) Increased protein kinase C and isozyme redistribution in pressure-overload cardiac hypertrophy in the rat. *Circ Res* 75:926-931.
7. Pass, J. M. et al. (2001) PKCepsilon activation induces dichotomous cardiac phenotypes and modulates PKCepsilon-RACK interactions and RACK expression. *Am J Physiol Heart Circ Physiol* 280:H946-955.
8. Montgomery, D. E. et al (2005) Protein kinase C epsilon induces systolic cardiac failure marked by exhausted inotropic reserve and intact Frank-Starling mechanism. *Am J Physiol Heart Circ Physiol* 289:H1881-1888.
9. Mochly-Rosen; D. et al. (2000) Cardiotrophic effects of protein kinase C epsilon: analysis by in vivo modulation of PKCepsilon translocation. *Circ Res* 86:1173-1179.

10. Takeishi, Y. et al. (2000) Transgenic overexpression of constitutively active protein kinase C epsilon causes concentric cardiac hypertrophy. *Circ Res* 86:1218-1223.
11. Klein, G. et al. (2005) Increased collagen deposition and diastolic dysfunction but preserved myocardial hypertrophy after pressure overload in mice lacking PKCepsilon. *Circ Res* 96:748-755.
12. Souroujon, M. C., and Mochly-Rosen, D. (1998) Peptide modulators of protein-protein interactions in intracellular signaling. *Nat Biotechnol* 16:919-924.
13. Mochly-Rosen, D. (1995) Localization of protein kinases by anchoring proteins: a theme in signal transduction. *Science* 268:247-251.
14. Chen, L. et al. (2001) Opposing cardioprotective actions and parallel hypertrophic effects of delta PKC and epsilon PKC. *Proc Natl Acad Sci USA* 98:11114-11119.
15. Chen, L. et al. (2001) Molecular transporters for peptides: delivery of a cardioprotective epsilonPKC agonist peptide into cells and intact ischemic heart using a transport system, R(7). *Chem Biol* 8:1123-1129.
16. Inagaki, K., and Mochly-Rosen, D. (2005) DeltaPKC-mediated activation of epsilonPKC in ethanol-induced cardiac protection from ischemia. *J Mol Cell Cardiol* 39:203-211.
17. Gray, M. O. et al. (1997) A selective epsilon-protein kinase C antagonist inhibits protection of cardiac myocytes from hypoxia-induced cell death. *J Biol Chem* 272:30945-30951.
18. Inagaki, K. et al. (2003) Additive protection of the ischemic heart ex vivo by combined treatment with delta-protein kinase C inhibitor and epsilon-protein kinase C activator. *Circulation* 108:869-875.
19. Inagaki, K. et al. (2005) Cardioprotection by epsilon-protein kinase C activation from ischemia: continuous delivery and antiarrhythmic effect of an epsilon-protein kinase C-activating peptide. *Circulation* 111:44-50.
20. Schwarze, S. R. et al. (1999) In vivo protein transduction: delivery of a biologically active protein into the mouse. *Science* 285:1569-1572.
21. Inoko, M. et al. (1994) Transition from compensatory hypertrophy to dilated, failing left ventricles in Dahl salt-sensitive rats. *Am J Physiol* 267:H2471-2482.
22. Tanaka, M. (1986) Quantitative analysis of myocardial fibrosis in normals, hypertensive hearts, and hypertrophic cardiomyopathy. *Br Heart J* 55:575-581.
23. Iwanaga, Y. (2004) Chronic phospholamban inhibition prevents progressive cardiac dysfunction and pathological remodeling after infarction in rats. *J Clin Invest* 113:727-736.
24. Livak, K. J., and Schmittgen, T. D. (2001) Analysis of relative gene expression data using real-time quantitative PCR and the 2(-Delta Delta C(T)) Method. *Methods* 25:402-408.
25. Iwanaga, Y. (1998) Cardiac endothelin-1 plays a critical role in the functional deterioration of left ventricles during the transition from compensatory hypertrophy to congestive heart failure in salt-sensitive hypertensive rats. *Circulation* 98:2065-2073.
26. Begley, R. (2004) Biodistribution of intracellularly acting peptides conjugated reversibly to Tat. *Biochem Biophys Res Commun* 318:949-954.
27. Brown, R. D. et al. (2005) The cardiac fibroblast: therapeutic target in myocardial remodeling and failure. *Annu Rev Pharmacol Toxicol* 45:657-687.
28. Katus, H. A. et al. (1991) Diagnostic efficiency of troponin T measurements in acute myocardial infarction. *Circulation* 83:902-912.
29. Dinarello, C. A. (1996) Biologic basis for interleukin-1 in disease. *Blood* 87:2095-2147.
30. Loppnow, H. et al. (1998) The interleukin-1 and interleukin-1 converting enzyme families in the cardiovascular system. *Eur Cytokine Netw* 9:675-680.
31. Iwanaga, Y. et al. (2002) Excessive activation of matrix metalloproteinases coincides with left ventricular remodeling during transition from hypertrophy to heart failure in hypertensive rats. *J Am Coll Cardiol* 39:1384-1391.
32. Thomas, C. V. et al. (1998) Increased matrix metalloproteinase activity and selective upregulation in LV myocardium from patients with end-stage dilated cardiomyopathy. *Circulation* 97:1708-1715.
33. Costello-Boerrigter, L. C. and Burnett, J. C., Jr. (2005) The prognostic value of N-terminal proB-type natriuretic peptide. *Nat Clin Pract Cardiovasc Med* 2:194-201.
34. Malhotra, A. et al. (2001) Angiotensin II promotes glucose-induced activation of cardiac protein kinase C isozymes and phosphorylation of troponin I. *Diabetes* 50:1918-1926.
35. Dostal, D. E. (1997) Molecular mechanisms of angiotensin II in modulating cardiac function: intracardiac effects and signal transduction pathways. *J Mol Cell Cardiol* 29:2893-2902.
36. Mascareno, E. and Siddiqui, M. A. (2000) The role of Jak/STAT signaling in heart tissue renin-angiotensin system. *Mol Cell Biochem* 212:171-175.
37. Itoh, H. et al. (2001) Differential effects of protein kinase C on human vascular smooth muscle cell proliferation and migration. *Am J Physiol Heart Circ Physiol* 281:H359-370.
38. Hishikawa, K. et al. (1994) Pressure promotes DNA synthesis in rat cultured vascular smooth muscle cells. *J Clin Invest* 93:1975-1980.
39. Rask-Madsen, C. and King, G. L. (2005) Proatherosclerotic mechanisms involving protein kinase C in diabetes and insulin resistance. *Arterioscler Thromb Vasc Biol* 25:487-496.
40. Testa, M. et al (1996) Circulating levels of cytokines and their endogenous modulators in patients with mild to severe congestive heart failure due to coronary artery disease or hypertension. *J Am Coll Cardiol* 28:964-971.
41. Mann, D. L. (2005) Targeted anticytokine therapy and the failing heart. *Am J Cardiol* 95:9C-16C; discussion 38C-40C.
42. Kumar, A. et al. (1996) Tumor necrosis factor alpha and interleukin 1beta are responsible for in vitro myocardial cell depression induced by human septic shock serum. *J Exp Med* 183:949-958.
43. Frantz, S. et al. (2003) Targeted deletion of caspase-1 reduces early mortality and left ventricular dilatation following myocardial infarction. *J Mol Cell Cardiol* 35:685-694.
44. Wang, X. et al. (2000) Expression of interleukin-1beta, interleukin-1 receptor, and interleukin-1 receptor antagonist mRNA in rat carotid artery after balloon angioplasty. *Biochem Biophys Res Commun* 271:138-143.
45. Rectenwald, J. E. (2000) Direct evidence for cytokine involvement in neointimal hyperplasia. *Circulation* 102:1697-1702.
46. Kirii, H. (2003) Lack of interleukin-1beta decreases the severity of atherosclerosis in ApoE-deficient mice. *Arterioscler Thromb Vasc Biol* 23:656-660.
47. Fields, L. E. (2004) The burden of adult hypertension in the United States 1999 to 2000: a rising tide. *Hypertension* 44:398-404.

48. Yancy, C. W. (2000) Heart failure in African Americans: a cardiovascular engima. *J Card Fail* 6:183-186.
49. Dhaliwal, A. and Thohan, V. (2006) Cardiac allograft vasculopathy: the Achilles' heel of long-term survival after cardiac transplantation. *Curr Atheroscler Rep* 8:119-130.
50. Braun, M. U. and Mochly-Rosen, D. (2003) Opposing effects of delta- and zeta-protein kinase C isozymes on cardiac fibroblast proliferation: use of isozyme-selective inhibitors. *J Mol Cell Cardiol* 35:895-903.
51. Distler, J. H. et al. (2007) Imatinib mesylate reduces production of extracellular matrix and prevents development of experimental dermal fibrosis. *Arthritis Rheum* 56:311-322.
52. Wakatsuki, T. et al. (2004) The biochemical response of the heart to hypertension and exercise. *Trends Biochem Sci* 29:609-617.
53. Jessup, M. and Brozena, S. (2003) *Heart failure. N Engl J Med* 348:2007-2018.
54. Schulz, R. (2007) Intracellular targets of matrix metalloproteinase-2 in cardiac disease: rationale and therapeutic approaches. *Annu Rev Pharmacol Toxicol* 47:211-242.
55. Brew, K. et al. (2000) Tissue inhibitors of metalloproteinases: evolution, structure and function. *Biochim Biophys Acta* 1477:267-283.

BRIEF SUMMARY

The following aspects and embodiments thereof described and illustrated below are meant to be exemplary and illustrative, not limiting in scope.

In one aspect, a method for slowing or inhibiting the progression of heart failure in a mammalian subject suffering from chronic hypertension is provided, comprising administering a therapeutically effective amount of an εPKC peptide inhibitor.

In some embodiments, the εPKC peptide inhibitor is from the V1 domain of εPKC. In particular embodiments, the εPKC peptide inhibitor is εV1-2.

In some embodiments, the εPKC peptide inhibitor is conjugated to a peptide that increases cellular uptake of the peptide inhibitor. In particular embodiments, the peptide that increases cellular uptake of the peptide inhibitor is TAT.

In some embodiments, εV1-2 is administered in combination with olmesartan.

In some embodiments, the mammalian subject is a heart transplant patient.

In another aspect, a method for slowing or inhibiting the progression of heart failure in a patients suffering from chronic hypertension is provided, comprising administering a therapeutically effective amount of an βIIPKC inhibitor.

In some embodiments, the βIIPKC inhibitor is from the V5 domain of βIIPKC. In particular embodiments, the βIIPKC peptide inhibitor is βIIV5-3.

In some embodiments, the βIIPKC peptide inhibitor is conjugated to a peptide that increases cellular uptake of the peptide inhibitor. In particular embodiments, the peptide that increases cellular uptake of the peptide inhibitor is TAT.

In some embodiments, the βV5-3 peptide inhibitor is administered in combination with olmesartan.

In some embodiments, the mammalian subject is a heart transplant patient.

In a related aspect, a method for slowing or inhibiting the progression of heart failure in a mammalian subject suffering from chronic hypertension, comprising administering a therapeutically effective amount of a PKC peptide inhibitor selected from εV1-2, βIV5-3, and βIIV5-3. In some embodiments, the PKC peptide is conjugated to a peptide that increases cellular uptake of the peptide inhibitor. In particular embodiments, the peptide that increases cellular uptake of the peptide inhibitor is TAT.

In some embodiments, the PKC peptide inhibitor is administered in combination with olmesartan.

In some embodiments, the mammalian subject is a heart transplant patient.

In addition to the exemplary aspects and embodiments described above, further aspects and embodiments will become apparent by reference to the drawings and by study of the following descriptions.

BRIEF DESCRIPTION OF THE DRAWINGS

FIG. 1E) and left ventricular weight to body weight ratio (LVW/BW; FIG. 1F) measured in 17-weeks old rats (n=6-8 per group).

FIGS. 10A and 10B share the same legend. The number of animals in each group is indicated.

BRIEF DESCRIPTION OF THE SEQUENCES

TAT peptide: YGRKKRRQRRR; SEQ ID NO: 1.
βIV5-3 PKC peptide inhibitor KLFIMN; SEQ ID NO: 2.
βIIV5-3 peptide inhibitor QEVIRN; SEQ ID NO: 3.
δV1-1 peptide inhibitor SFNSYELGSL; SEQ ID NO: 4.
εV1-2 PKC peptide inhibitor EAVSLKPT; SEQ ID NO: 5.
ψεRACK HDAPIGYD; SEQ ID NO: 6.

Antennapedia peptide: RQIKIWFQNRRMKWKK; SEQ ID NO: 7.

DETAILED DESCRIPTION

In one aspect, a treatment method is provided for slowing or inhibiting the progression of heart failure in a mammalian subject, e.g., a mammalian patient, suffering from chronic hypertension. The method is based on the finding that pharmacological inhibition of εPKC is beneficial and activation of εPKC is deleterious in transition to heart failure, as will be illustrated in the studies described herein, below. The effective amount and administration schedule of the εPKC inhibitor are determined based on the animal experiments described herein and the knowledge of those skilled in the art.

A related aspect of the method is based on the finding that pharmacological inhibition of βIIPKC and, to a lesser extent, a βIPKC, is beneficial in transition to heart failure, as will be illustrated in the studies described herein, below. The effective amount and administration schedule of the βIIPKC inhibitor and βIPKC inhibitor are determined based on the animal experiments described herein and the knowledge of those skilled in the art.

I. εPKC Inhibitors

In one aspect, the methods include administering a peptide from the V1 domain of εPKC to slow or the progression of heart failure. An exemplary peptide is the εV1-2 peptide.

Experimental data show that εPKC levels and activity increase in Dahl rats fed on high-salt diet (HS) at the age of 11 weeks, and by 17 weeks decrease to the same levels as rats fed with a low-salt diet (0.3% NaCl; LS) (3). To determine whether εPKC plays any role in the transition to heart failure and death, HS rats were treated with the selective εPKC inhibiting peptide, $TAT_{47-57}$-εV1-2 (εV1-2; 2.8 µg/kg/day using a subcutaneous Alzet pump (26)) or with saline as a control (HS-control) from the age of 11 weeks (when compensatory hypertrophy is seen) to 17 weeks (when heart failure is apparent; FIG. 1A)). Another group of hypertensive rats was treated for the same period with a common clinical treatment, the angiotensin II receptor type 1 blocker (ARB, olmesartan, Olm; 3 mg/kg/day).

Figure 7:
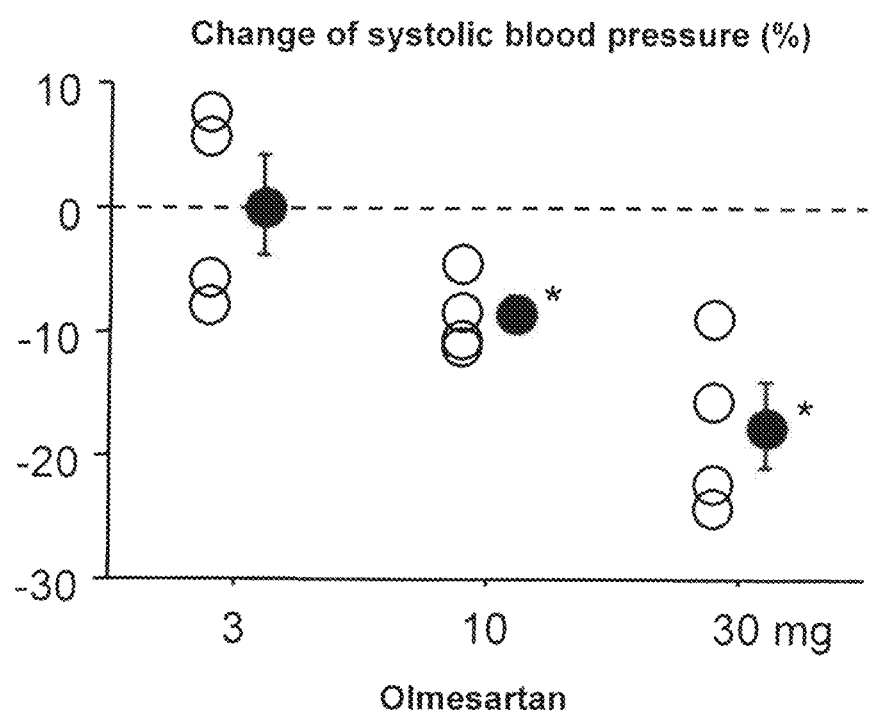
FIG. 7 shows the effect of olmesartan on systolic blood pressure of Dahl salt sensitive rats, where the change of systolic blood pressure, in percent, is shown as a function of olmesartan concentration, in mg.

Since only olmesartan has been shown to reduce blood pressure and since a decrease in blood pressure results in a reduced incidence of the disease, an olmesartan dose of only 3 mg was chosen. This dose does not affect systolic blood pressure in this model (FIG. 7), but is still beneficial to the heart (see below). Note that in a clinical setting, the administration of an angiotensin II receptor blocker causes reduced blood pressure, precluding the administration of large amounts of olmesartan. The present study is primarily designed to look at the blood pressure-independent effects of the inhibitor peptides.

The effects of all these treatments were compared to those of HS-control (HS-C) or LS-control (LS-C) by evaluating survival rate and cardiac function, as measured by fractional shortening, lung weight, left ventricle weight and systolic blood pressure (FIGS. 1B-1G).

Figure 8:
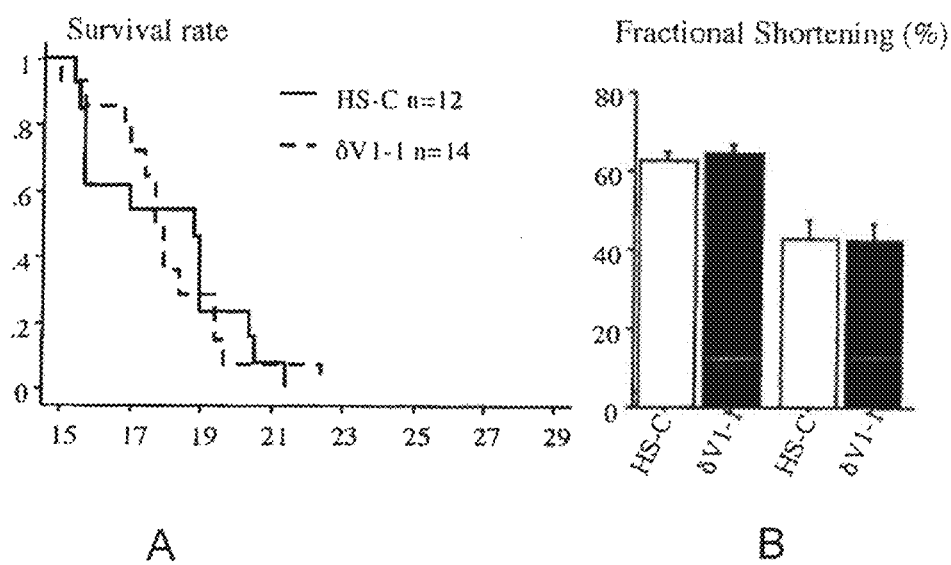
FIGS. 8A and 8B shows the survival rate as a function of time (FIG. 8A) and the fractional shortening, in percent (FIG. 8B), for rats with hypertension-induced heart failure and treated with δPKC inhibitor, $TAT_{47-57}$-δV1-1.
Figure 10:
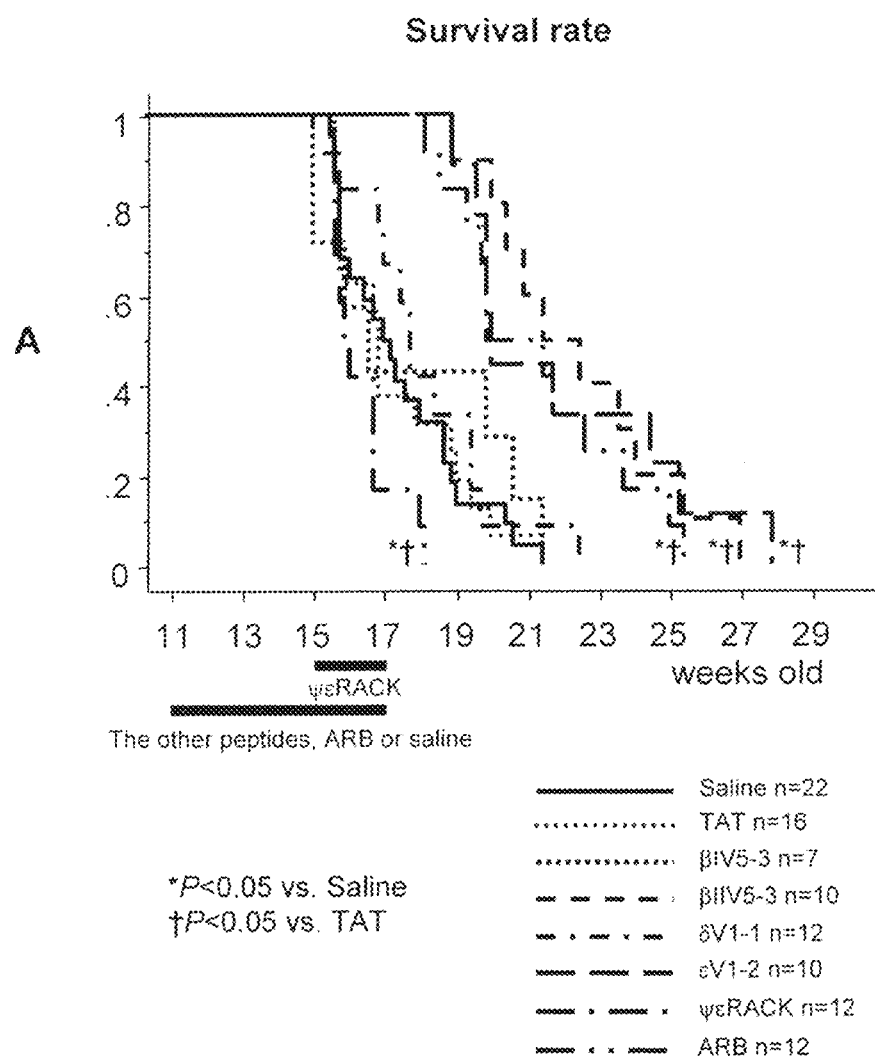
FIGS. 10A and 10B show the survival rate from heart failure in rodents as a function of rodent age (FIG. 10A) and the blood pressure (FIG. 10B) in animals treated with saline, TAT peptide, a βIV5-3 PKC peptide inhibitor, a βIIV5-3 peptide inhibitor, δV1-1 peptide inhibitor, εV1-2 PKC peptide inhibitor, ΨεCRACK, an εPKC activator, and angiotensin 11 receptor blocker.
Figure 10:
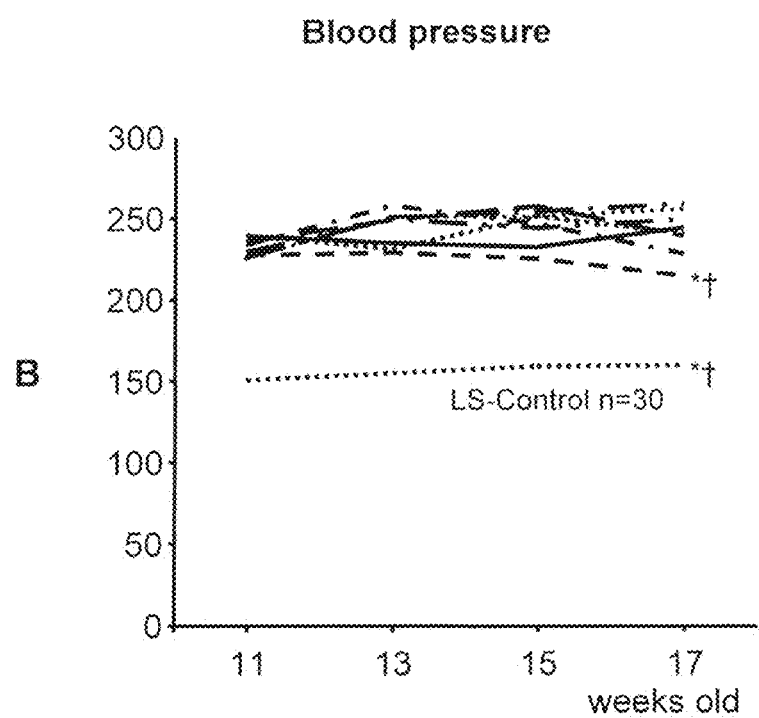

Dahl salt-sensitive rats on high-salt diet (HS) developed heart failure, as evidenced by a decreased fractional shortening and increased lung weight to body weight ratio (LungW/BW), left ventricular weight to body weight ratio (LV/BW) and systolic blood pressure as compared with LS-control, and they died from heart failure between the ages of 15 to 21 weeks (FIGS. 1B-1G, Table 1). Chronic treatment with the $TAT_{47-57}$-εV1-2 or olmesartan improved survival rate, maintained normal fractional shortening, and prevented the increase in lung weight/BW at 17 weeks old, indicating that theses treatments prevented the progression of heart failure (FIG. 1B-1E, Table 1). Because previous studies suggested that the δ and εPKC have similar roles in developmental hypertrophy (14), the effect of the εPKC-selective inhibitor, TAT$_{47-57}$-δV1-1 (14), in this model was also determined. A six-week treatment with δV1-1 between 11 and 17 weeks did not improve cardiac function nor did it affect heart failure survival (FIGS. 1, 8, and 10), indicating the selective protective effect of the εPKC inhibitor during the progression to heart failure.

selectively regulates the translocation of εPKC. In addition, these results suggest that chronic treatment with ARB maintained cardiac function via a mechanism other than the εPKC pathway.

As shown above, εPKC inhibition and olmesartan prevents the progression to heart failure. Studies were also conducted to determine whether cardiac fibrosis, a histological sign of myocardial remodeling and inflammation in the injured and failing myocardium (27), was also inhibited by εPKC inhibition. To visualize cardiac fibrosis, left ventricle tissues from

TABLE 1

Body weight and in vivo echocardiographic data

| Group | n | BW (g) | PWT (mm) | EDD (mm) | ESD (mm) | FS (%) | Systolic Wall Stress (g/cm$^2$) |
|---|---|---|---|---|---|---|---|
| LS-C | 25 | 428.5 ± 4.5 | 1.4 ± 0.04 | 7.0 ± 0.1 | 2.8 ± 0.2 | 60.4 ± 1.9 | 29.1 ± 3.3 |
| HS-C | 8 | 366.6 ± 11.4* | 1.5 ± 0.03 | 8.3 ± 0.6* | 5.1 ± 0.7* | 43.5 ± 6.0* | 92.0 ± 24.9* |
| ΨεR | 13 | 343.5 ± 16.4* | 1.6 ± 0.06 | 8.2 ± 0.3* | 4.9 ± 0.5* | 41.1 ± 3.5* | 131.1 ± 20.2* |
| εV1-2 | 10 | 382.0 ± 6.6* | 1.5 ± 0.03 | 7.1 ± 0.1† | 3.0 ± 0.2† | 58.4 ± 2.2† | 35.0 ± 3.8† |
| Olm | 12 | 385.4 ± 10.8* | 1.5 ± 0.04 | 7.3 ± 0.2† | 3.1 ± 0.2† | 58.4 ± 1.6† | 50.7 ± 4.4† |

Body weight (BW) and echocardiographic data were measured at 17 weeks of age. LS-C—control rats fed with low-salt diet; HS-C—saline-treated rats fed with high-salt diet; ΨεR—rats treated with the εPKC activator, TAT$_{47-57}$-ΨεRACK, from 15 to 17 weeks of age; εV1-2—rats treated with the εPKC inhibitor, TAT$_{47-57}$-εV1-2, from 11 to 17 weeks of age; Olm—rats treated with angiotensin II receptor blocker, olmesartan, from 11 to 17 weeks of age; PWT—LV posterior wall thickness; EDD—LV end-diastolic diameter; ESD—LV end-systolic diameter, FS—LV fractional shortening. Systolic wall stress is calculated according to the formula (SBP × ESD)/[4 × PWT × (1 + PWT/ESD)]. Values are mean ± SEM.
*P < 0.05 vs. LS-C;
†P < 0.05 vs. HS-C.

Because εPKC inhibition during the transition to heart failure is protective, εPKC activation may be deleterious. To examine this directly, HS rats were also treated with the selective εPKC activating peptide, TAT$_{47-57}$-ΨεRACK (Ψε-RACK; 2.8 μg/kg/day). Since εPKC activity and level decreased in the failing heart by 17 weeks (3), the εPKC activator was only delivered between 15 and 17 weeks and the outcome on heart failure and survival were determined (FIG. 1A). Treatment with TAT$_{47-57}$-ΨεRACK accelerated the death rate (FIG. 1B). There was also a trend towards a reduced fractional shortening at the age of 17 weeks relative to HS-control and a statistically significant reduction relative to LS age-matched control Dahl salt-sensitive rats (FIG. 1D, Table 1). None of the treatments affected systolic blood pressure (FIG. 1G) and therefore, there was no difference in the extent of pressure overload between the groups. These data indicate that chronic treatment with the εPKC inhibitor or angiotensin II receptor blocker, olmesartan, protects the heart from pressure-overload-induced heart failure in hypertensive rats, whereas prolonged treatment with the εPKC activator appears to accelerate the transition from compensatory hypertrophy to heart failure.

Figure 2:
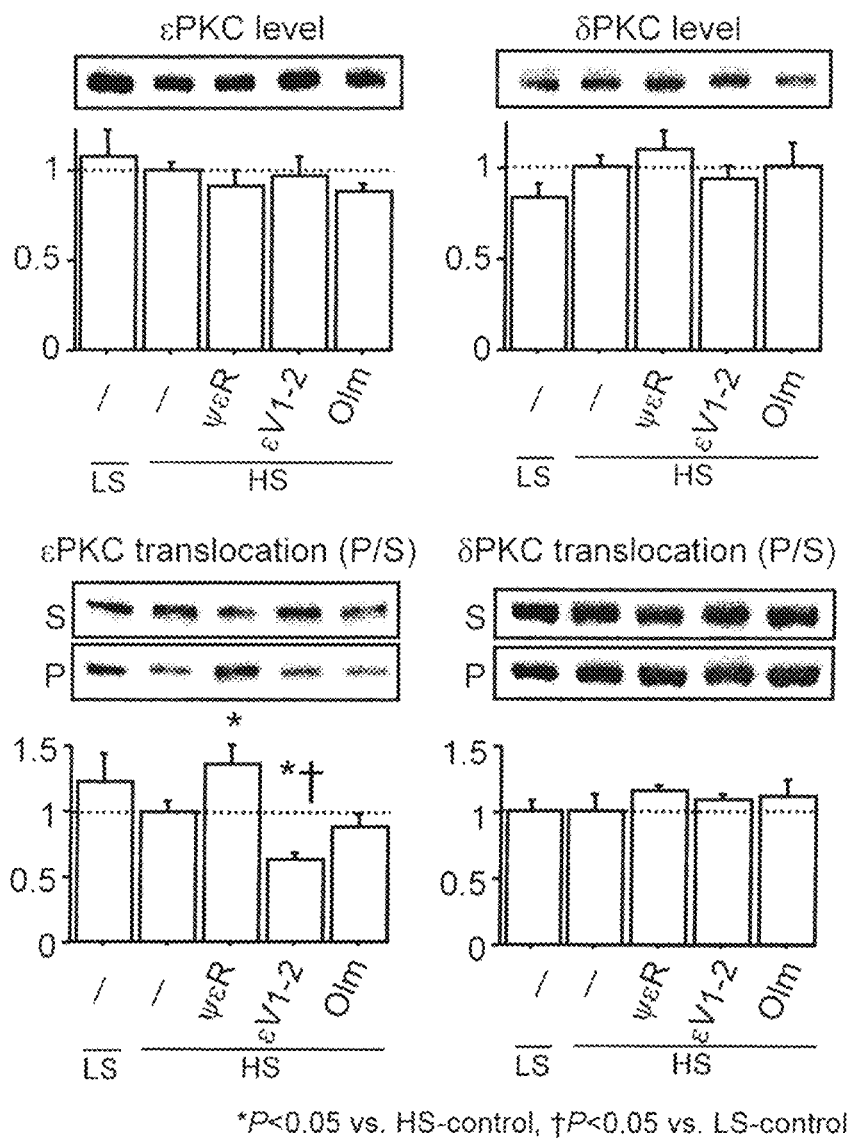
FIG. 2 shows the levels and translocation of ε and δPKC in left ventricle tissues from 17-week-old rats by western blots (n=6 per group). Data are shown as a ratio to low-salt control (LS-C). P and S indicate particulate and soluble fraction, respectively. *$P<0.05$ vs. LS-C, †$P<0.05$ vs. HS-C.
Figure 3:
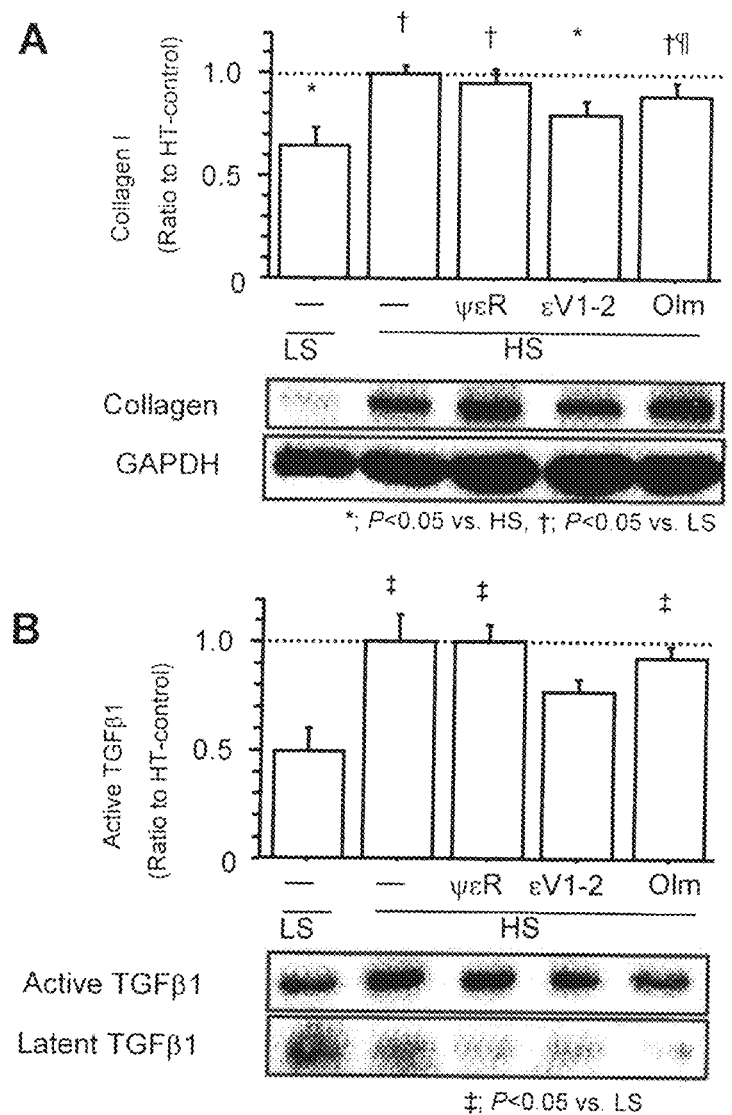
FIG. 3A-3D show regulation of fibrosis by εPKC during Heart Failure. (A), Left ventricle tissues from 17-week-old rats were stained with Masson's trichrome to assess cardiac fibrosis (not shown). Corresponding tissue was analyzed for collagen expression, levels of active TGFβ1, net-MMP2 activity, and collagen secretion, as described in the text. (A) Collagen expression in LV tissue in same samples for panel A (n=6). Lower panel; representative pictures for each blot. (B) Active TGFβ1 level was presented as ratio of active dimer form (25 kDa) vs. latent form (39 kDa). Lower panel; representative pictures for each blot. (C) Net MMP2 activity was presented as ratio of MMP2 activity from zymography divided by TIMP2 level from western blotting (n=6). Lower panel; representative pictures for each measurement. (D) Collagen secretion from cultured primary cardiac fibroblast is presented as ratio to no TGFβ treatment (n=3).
Figure 3:
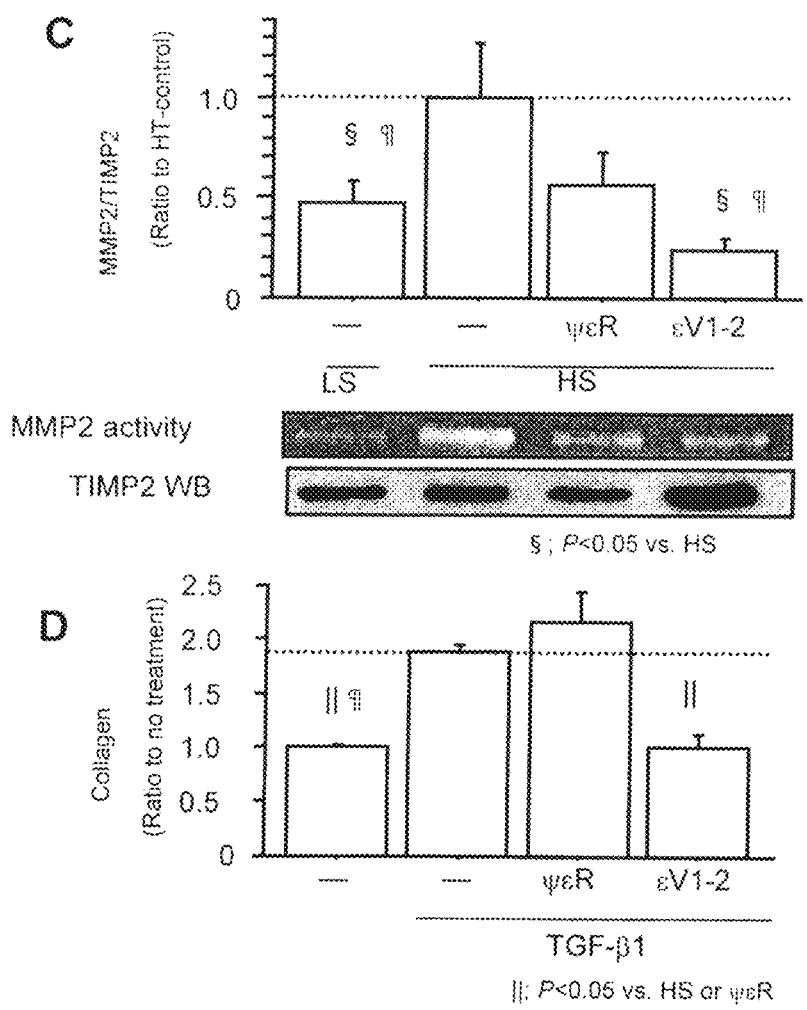

In another series of studies, it was shown that sustained pharmacological inhibition or activation of εPKC does not alter the expression of εPKC, but affects its translocation. The selective effects of the εPKC inhibitor, TAT$_{47-57}$-εV1-2, and the εPKC activator, TAT$_{47-57}$-ΨεRACK were confirmed by western blot analysis of left ventricle (LV) tissues from chronically-treated 17-week-old hypertensive rats. Neither treatment significantly affected the total levels of εPKC or δPKC, as compared with HS-control animals (FIG. 2, upper panels). The levels of εPKC in the particulate fraction were significantly lower in TAT$_{47-57}$-εV1-2-treated rats as compared with the HS-control rats, but the levels of δPKC in that fraction were unaffected. Similarly, sustained treatment with the εPKC translocation activator increased the levels of εPKC in the particulate fraction relative to the HS-control rats, but did not affect the levels of δPKC (FIG. 2 lower panels). Finally, treatment with olmesartan did not affect the expression or distribution of εPKC or δPKC (FIG. 2). Thus, the treatment with the εPKC inhibitor or the εPKC activator 17-week-old rats were stained with Masson's trichrome staining (not shown). Chronic treatment with the εPKC inhibitor, TAT$_{47-57}$-εV1-2, or olmesartan reduced fibrosis in LV by ~50% as compared with HS-control. Conversely, a two-week treatment with the εPKC activator, TAT$_{47-57}$-Ψε-RACK, increased fibrosis by ~150% as compared with HS-control (FIG. 3). Thus, the pharmacological regulation of εPKC or ARB on heart failure correlated with the expected regulation of cardiac fibrosis.

The level of collagen I in tissue homogenate was significantly decreased in the εV1-2-treated group when compared to HS-control group (FIG. 3A). One of the major pro-fibrotic cytokines, TGFβ1, also increased in the hypertensive group, and this was partially reversed by εV1-2 treatment (FIG. 3B). Thus, expression and levels of TGFβ1 and collagen correlated well with the extent of tissue fibrosis.

Matrix metalloproteinases (MMPs) regulate cardiac fibrosis and remodeling and therefore we reasoned that their levels may be regulated in this heart failure model. We measured MMP activity using zymography and found that the levels of MMP2, one of the major MMPs regulating heart failure (31), was increased in the hypertensive rats (250%±20 compared to normotensive control rats). Unexpectedly, the increase in MMP2 was attenuated by both the εPKC activator and εPKC inhibitor (FIG. 3C). The activity of other MMPs, such as MMP9, was below detectable levels, supporting the findings that MMP2 is the most abundant MMP in the failing heart (54). Because of its relative specificity for MMP2 as compared with other TIMPs (55), we next determined whether TIMP2 was differentially affected by the εPKC regulators (FIG. 3C). TIMP2 level was increased in εV1-2 treated group relative to all the other groups. Therefore, when expressed as a ratio of MMP2 to TIMP2 levels, we found that εV1-2 treatment of hypertensive rats significantly decreased the ratio of MMP2/TIMP2 as compared with that in control hypertensive rats, likely resulting in reduced MMP2 activity in the tissue.

To further address the question whether εPKC controls cardiac fibroblasts directly or regulates upstream fibrosis-inducing events, we carried out an in vitro collagen secretion assay using cultured cardiac fibroblasts (FIG. 3D). Collagen secretion into the cell culture media increased with TGFβ treatment and εV1-2 inhibited this effect, whereas εPKC activation (by ΨεRACK) resulted in a trend to enhance TGFβ-induced collagen secretion. Since εV1-2 treatment did not affect collagen secretion under basal conditions (data not shown), the data suggest that εPKC may further contribute to heart failure progression, at least in part, by enhancing TGFβ-induced collagen release.

Figure 4:
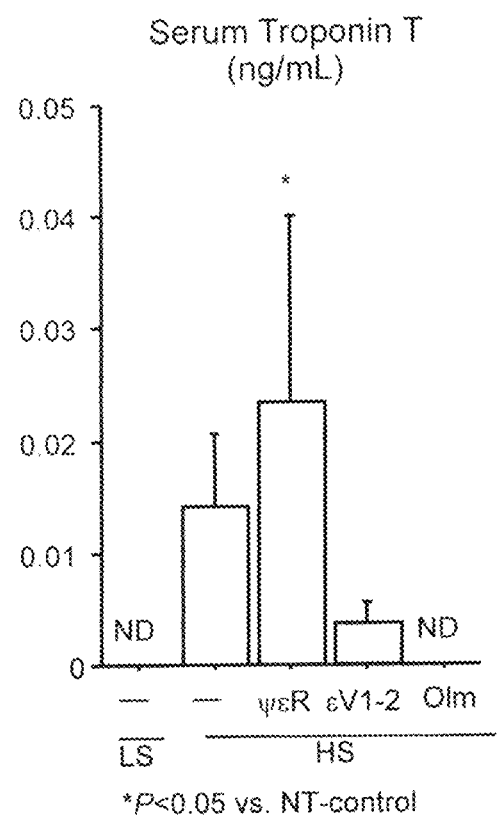
FIG. 4 shows the serum levels of troponin T determined in 17-week-old rats treated with Olm, εV1-2, ΨεRACK, or vehicle (n=8-15). Serum troponin T was not detected in LS-C and olmesartan-treated rats. *$P<0.05$ vs. LS-C.

Chronic treatment with TAT$_{47-57}$-ΨεRACK induced arterial stenosis and increased fibrosis around the arteries (FIG. 4). To determine whether arterial occlusion by stenosis leads to cardiac ischemia and myocardial infarction in the hypertensive rats treated with the εPKC-activator, the serum concentration of troponin T, a marker of myocardial cell damage in patients with acute myocardial infarction was measured (28). Serum troponin T was not detected in LS-control rats and in the olmesartan-treated rats. However, serum troponin T levels significantly increased in ΨεRACK-treated rats as compared to LS-control. Importantly, treatment with TAT$_{47-57}$-ΨεRACK did not cause arterial stenosis in normotensive Dahl salt-sensitive rats on a low-salt diet (not shown), indicating the selectivity of the εPKC activator's effect on hypertensive rats. Arterial stenosis and fibrosis due to sustained activation of εPKC may accelerate cardiac damage and progression to heart failure, possibly due to increased occurrence of myocardial ischemia.

In another study, the effects of pharmacological inhibition or activation of εPKC and olmesartan on gene expression profile was analyzed. To address the molecular differences in the protective effects induced by εPKC inhibition and olmesartan, real-time PCR was used to monitor changes in gene expression resulting from each treatment. The effects of chronic treatment (as above) with the εPKC inhibitor (TAT$_{47-57}$-εV1-2), the εPKC activator (TAT$_{47-57}$-ΨεRACK) or olmesartan (ARB) in LV from 17-week-old rats on the expression of 92 genes was examined. These include genes encoding neurohormones, cytokines, growth factors, cell signaling proteins, apoptosis-related proteins, sarcoplasmic reticulum-related proteins, contractile proteins, oxidative stress-related proteins, nitric oxide-related proteins, extracellular matrix-related enzymes, and cytoskeletal proteins, which are proposed to have roles in heart failure or in PKC signaling (see Supplementary Methods Table).

The treatment with TAT$_{47-57}$-εV1-2, but not olmesartan, modified the expression of 10 genes, including hormone receptors (AT1 receptor, AT2 receptor, β1-adrenergic receptor, calcitonin receptor), growth factors (HGF, VEGF), IL-1β, calcineurin B, iNOS and troponin I (FIGS. 5A-5B). The treatment with ARB, but not with εV1-2, modified the expression of 15 genes, including those encoding apoptosis-related proteins (BAX, Bcl-2), oxidative stress-related proteins (p22phox, p47phox, p67phox, SOD2), cardiotrophin-1, receptor for activated C-kinase-1 (RACK1), calcineurin A, STAT1, caveolin-2, RelA, phospholamban, troponin C and desmin (FIG. 5A). Thus, sustained inhibition of εPKC in hypertensive animals during transition to heart failure modified the expression of genes related to receptors and growth factors, while the treatment with ARB modified the expression of genes related to apoptosis and oxidative stress. These data suggest that the εPKC inhibitor and ARB prevent the progression of heart failure at least partially via different mechanisms.

The treatment with TAT$_{47-57}$-ΨεRACK increased gene expression of several genes including the cytokines IL-1β and IL-6 and the genes encoding extracellular matrix related enzymes including MMP7 and TIMP1 (FIG. 5C, Table 3). Increased expression of cytokines may contribute to coronary arterial damage (29, 30) and increased expression of extracellular matrix-related enzymes may induce cardiac remodeling (31, 32). These data suggest that modification in expression of these genes may contribute to the progression of heart failure and/or to arterial stenosis in the εPKC activator-treated hearts.

There was an overlapping change in expression of only three genes when comparing the TAT$_{47-57}$-εV1-2-treated group with the olmesartan-treated group (FIG. 5A, Venn diagram): those encoding ANP and endothelin-1 precursors and nitric oxide synthase (nNOS). Since individual animals within each treatment group did not exhibit identical cardiac functions and changes in gene expression, it was determined whether there was an overall correlation between the two parameters. The decline in the expression of the precursor of ANP and precursor of endothelin 1 appears to be inversely correlated with improved cardiac function ($r=0.410$, $P=0.0273$ for the ANP precursor and $r=0.568$, $P=0.0011$ for prepro-endothelin-1; $n=30$; FIGS. 5A, 5D). The increase in neuronal nitric oxide appears to correlate directly with improved cardiac function ($r=0.566$, $P=0.0011$; $n=30$; FIGS. 5A, 5D). Further, serum BNP, an established marker of heart failure in humans (33), appeared to inversely correlate with improved fractional shortening ($r=0.529$, $P<0.0027$; $n=30$; FIG. 5D).

In another study, it was established that a combined treatment with the εPKC inhibitor and ARB during the transition from compensatory hypertrophy to heart failure is superior to treatment with ARB alone. A combination treatment with the εPKC inhibitor (TAT$_{47-57}$-εV1-2) and ARB (olmesartan) in the hypertension-induced heart failure model shows greater protection. Treatment of the hypertensive rats from the age of 11 to 19 weeks with TAT$_{47-57}$-εV1-2 together with olmesartan ($n=12$; FIG. 6A) improved survival rate as compared with the treatment of olmesartan alone for the same period, and maintained normal fractional shortening (compared to LS control; FIG. 1B) even in 24 week-old rats without reducing blood pressure (FIG. 6B-6D, Table 2). Furthermore, 40% of the animals with the combined treatment survived for up to 35 weeks, even though the treatment was stopped 16 weeks earlier (FIG. 6B). Therefore, the presence of both the εPKC inhibitor and ARB prevent the progression of heart failure via different mechanisms and the protective effect during the critical time of transition to heart failure appears to last for many weeks even in the absence of continuous treatment.

TABLE 2

Body weight and in vivo echocardiographic data

| Group | n | BW (g) | PWT (mm) | EDD (mm) | ESD (mm) | FS (%) | Systolic Wall Stress (g/cm$^2$) |
|---|---|---|---|---|---|---|---|
| Olm | 6 | 422.5 ± 15.1 | 1.5 ± 0.03 | 7.9 ± 0.2 | 4.9 ± 0.5 | 38.3 ± 4.6 | 105.8 ± 13.6 |
| Olm + εV1-2 | 7 | 432.9 ± 13.1 | 1.5 ± 0.04 | 7.2 ± 0.1* | 3.4 ± 0.3* | 53.5 ± 3.7* | 54.7 ± 7.2 |

Body weight (BW) and echocardiographic data were measured at 24 weeks of age. Olm—rats treated with angiotensin II receptor blocker, olmesartan, from 11 to 19 weeks of age; Olm + εV1-2—rats treated with both olmesartan and the εPKC inhibitor, TAT$_{47-57}$-εV1-2, from 11 to 19 weeks of age; PWT—LV posterior wall thickness; EDD—LV end-diastolic diameter; ESD—LV end-systolic diameter; FS—LV fractional shortening. Systolic wall stress is calculated as (SBP × ESD)/[4 × PWT × (1 + PWT/ESD)].
Values are mean ± SEM.
*P < 0.05 vs. Olm.

In summary, the studies herein demonstrate that pharmacological inhibition of εPKC, during the transition from compensatory cardiac hypertrophy to heart failure, slowed the progression of heart failure. Pharmacological activation of εPKC for only two weeks, just between 15 and 17 weeks of age, accelerated the progression of heart failure and fibrosis and caused arterial stenosis in the hypertensive rats. Furthermore, the combined treatment with an εPKC inhibitor and an established clinical treatment for human heart failure (2), ARB, have beneficial effects in improving survival rate and maintaining cardiac function relative to ARB alone. It should be noted that although angiotensin II activates εPKC, other PKC isozymes (34) and JAK/STAT signaling (35, 36) are also activated. This may explain why the εPKC inhibitor together with angiotensin II inhibitor produce beneficial effects. Indeed, gene expression profiling confirmed select effects of each of these protective treatments.

The studies also demonstrate that εPKC activation in hypertensive rats increased arterial stenosis. Although previous studies demonstrated that the activation of PKC induced proliferation of vascular smooth muscle cells, in vitro (37, 38), the role of εPKC in arterial stenosis in vivo has not been described before (39). Interestingly, εPKC activation in naïve animals produces protection from an ischemic event by inducing preconditioning-mimetic effects without causing adverse effects in either mice (26) or rats.

Cardiac remodeling is an important feature of heart failure and a potential target for new therapeutics (52,53). The histological analysis of cardiac tissue showed reduced fibrosis with εPKC inhibition. Since we found previously that εPKC inhibition does not affect fibroblast proliferation (50), we hypothesized that εPKC may control another feature of fibroblasts that contributes to the effect on fibrosis. Indeed, the ratio of latent to active TGFβ was regulated by εPKC and in the in vitro culture experiment, εPKC inhibition abrogated TGFβ-induced collagen secretion. Together, those changes in active TGFβ levels and collagen secretion may account for the decrease in collagen accumulation and fibrosis in the hypertensive rats treated with the εPKC inhibitor.

Figure 5:
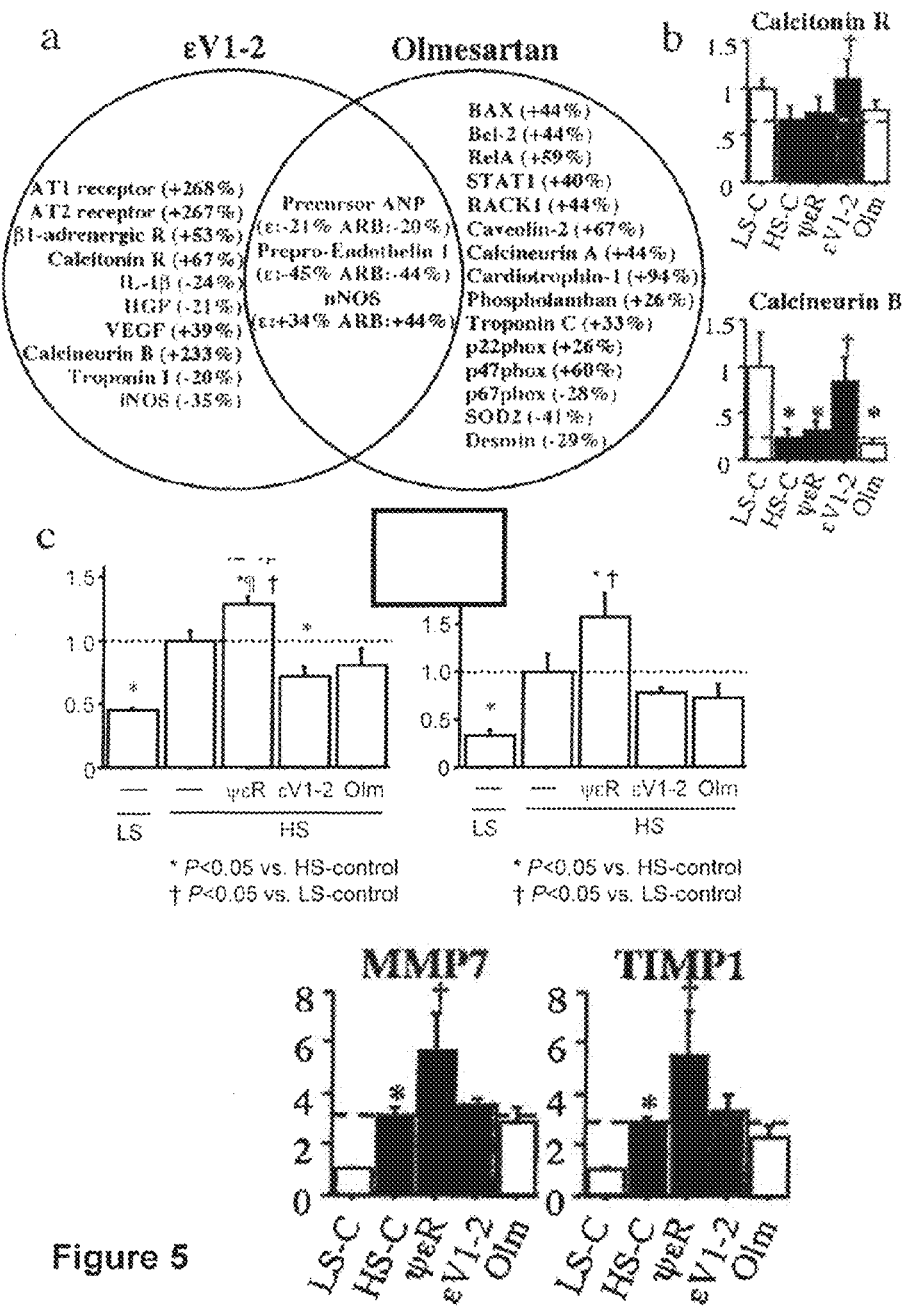
FIG. 5A shows that treatment with the PKC inhibitor, $TAT_{47-57}$-εV1-2 (εV1-2), or with the angiotensin II receptor blocker, olmesartan (Olm), modified gene expression as determined using real-time PCR in left ventricle tissues from 17-week-old rats (n=6 for group). The expression of genes indicated in red were significantly increased and the expression of genes indicated in green were significantly reduced, as compared with HS-C. The percent increase or decrease is provided in parentheses.
FIG. 5B shows that εV1-2 maintained expression of calcitonin receptor and calcineurin B.
FIG. 5C shows that Treatment with the εPKC activator, $TAT_{47-57}$-ΨεRACK (ΨεR) increased expression of IL-1β, IL-6, MMP7 and TIMP1. Data are shown as ratio to LS-C.
FIG. 5D shows that the precursor ANP, precursor BNP and prepro-endothelin 1 expression correlated negatively with fractional shortening. Neuronal nitric oxide synthase (nNOS) correlated positively with fractional shortening. *$P<0.05$ vs. LS-C, †$P<0.05$ vs. HS-C.
Figure 5:
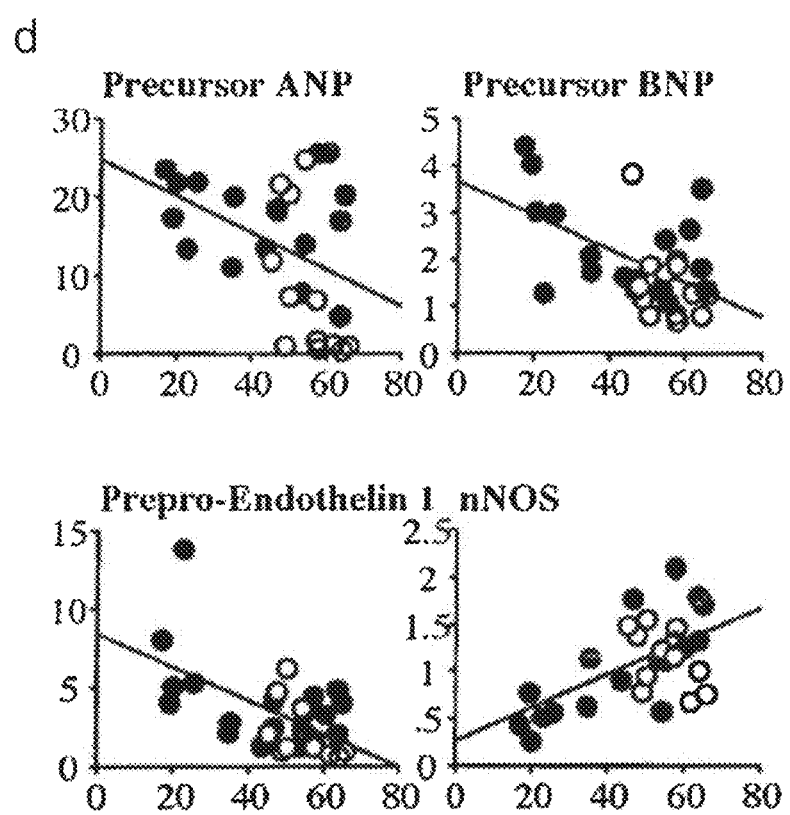

Gene expression profiling identified potential downstream regulators of the response to heart failure. Both a change in expression of cytokines and a change in expression of extracellular matrix enzymes were observed. Pro-inflammatory cytokines, including IL-1β, are elevated in the plasma of patients with chronic heart failure (40). However, whether pro-inflammatory cytokines play a role in the pathogenesis of heart failure in humans is not clear (41). The studies herein show that expression of IL-1β increased by treatment with an εPKC activator and decreased with an εPKC inhibitor (FIG. 5). IL-1β has negative inotropic effects (42) and may contribute to heart failure by promoting inflammation and cardiomyocyte apoptosis (43). In addition to its role in inflammation, IL-1β may contribute to neointimal formation and atherosclerosis in vascular disease (29, 30). Following injury, IL-1β is expressed at sites of active proliferation and migration of vascular smooth muscle cells (29, 44). Further, IL-1 type I receptor gene-deficient mice tend to develop less neointima (45), and the lack of IL-1β causes a decrease in the severity of atherosclerosis in apoE-deficient mice (46). Therefore, activation of εPKC may cause increased arterial stenosis and myocyte damage via increased transcription of these cytokines.

Previous studies demonstrated that the expression of MMPs and TIMPs is increased in failing hearts and suggested that an imbalance between MMPs and TIMPs might induce cardiac remodeling (31, 32). Chronic treatment with an εPKC activator also increased expression of genes involved in extracellular matrix regulation, specifically MMP7 and TIMP1 (FIG. 5C). However, neither εPKC inhibition nor ARB treatment appears to inhibit hypertension-induced increases in the expression of these genes. Therefore, εPKC-induced increase in fibrosis may be a consequence of the increased arterial stenosis and cardiac ischemia rather then a direct effect on the transcription of these genes.

We also examined the effect of εPKC on the ratio of MMP2 level to the level of inhibitor, TIMP2. εPKC inhibition reduced this ratio, which should result in a net decrease in MMP2 activity (FIG. 3C). However, although εPKC activation caused severe parenchymal fibrosis, the net-MMP2 activity showed also a trend (not significant) towards decreased MMP2 activity. These data may reflect the timing of sample analysis and the extent sclerosis-induced ischemia in the εPKC activator-treated animals. Therefore, it is possible that εPKC modulates cardiac fibrosis also by regulating metalloproteases.

Figure 6:
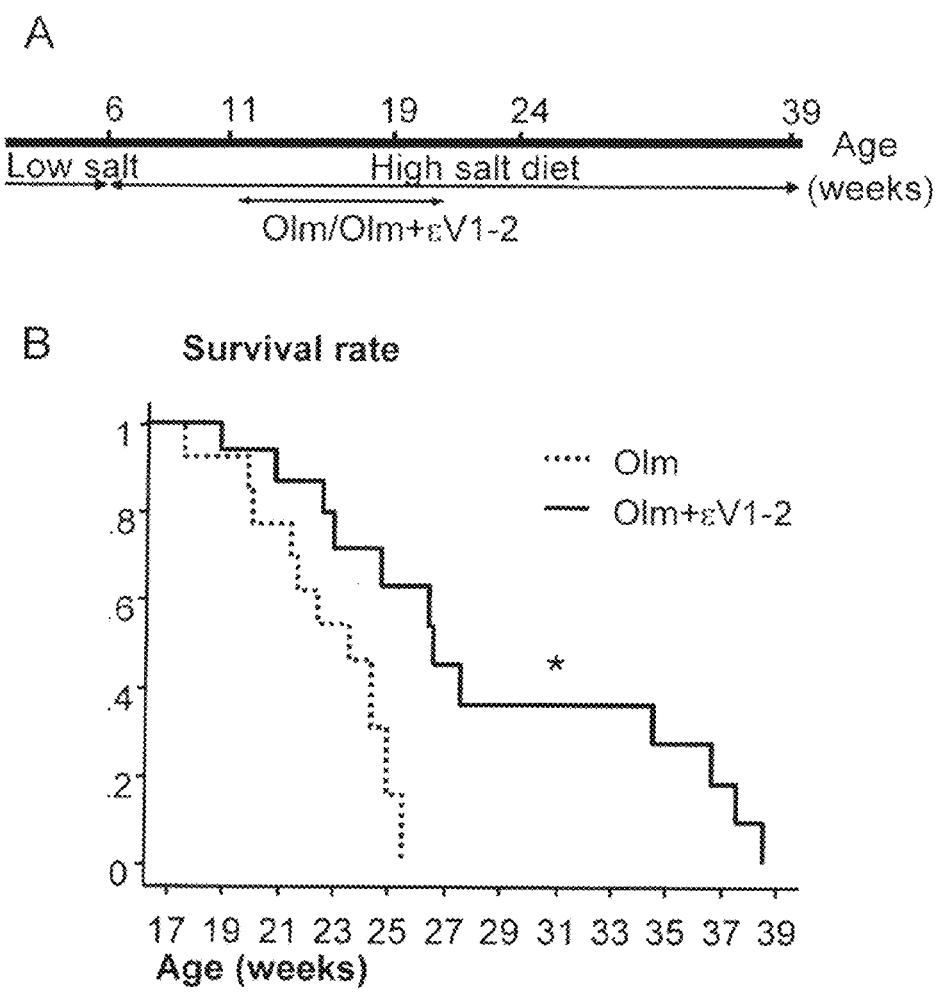
FIG. 6A shows a scheme for the protocol of treatments.
FIG. 6B shows the survival rate of rats with hypertension-induced heart failure treated with the εPKC inhibitor, $TAT_{47-57}$-εV1-2 (εV1-2), together with the angiotensin II receptor blocker, olmesartan (Olm, n=12), or Olm alone (n=13).
FIGS. 6C and 6D show fractional shortening in 19 and 24-week old rats, and systolic blood pressure at the age of 11, 15, 19 and 24 weeks, respectively. *$P<0.05$ vs. Olm, alone.
Figure 6:
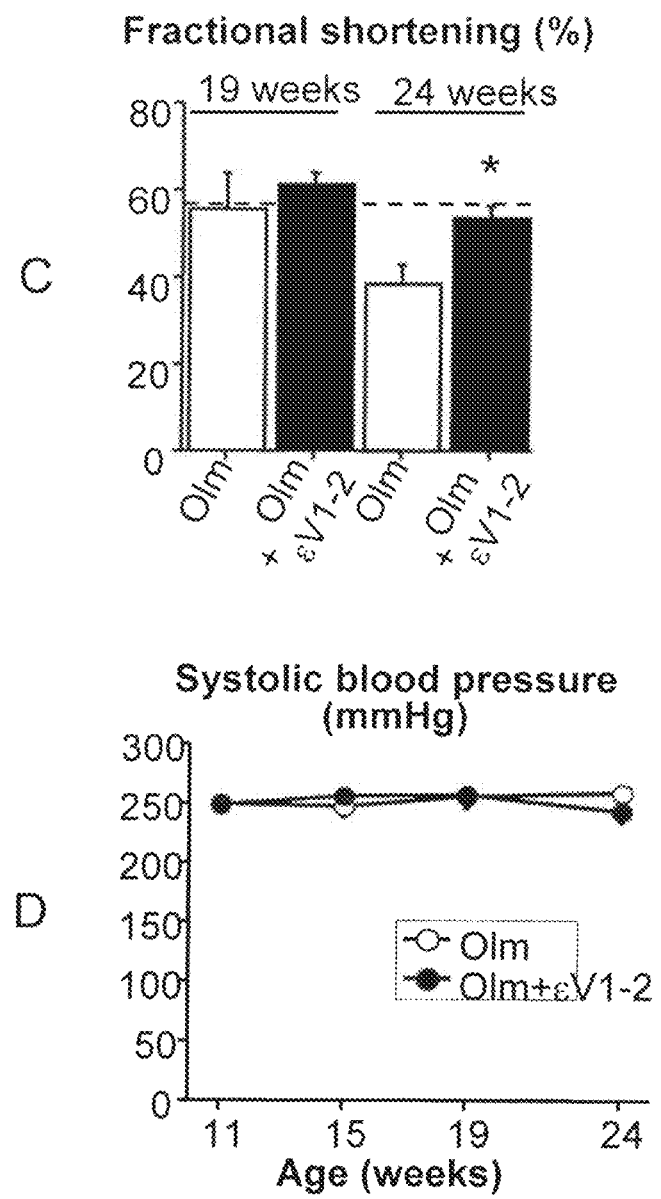

A combined treatment with $TAT_{47-57}$-εV1-2 and olmesartan was superior to treatment with olmesartan alone (FIG. 6). An εPKC inhibitor can augment current therapeutic strategies for the treatment of heart failure in humans. In addition, the coronary stenosis in hypertensive hearts caused by sustained activation of εPKC raises the possibility that sustained inhibition of εPKC may decrease vascular disease such as that observed in cardiac vasculopathy in transplanted hearts (49) and in patients with atherosclerosis.

Finally, inhibition of εPKC may be beneficial in the setting of heart failure and the consequent remodeling, in part, through regulation of fibrosis, collagen release from fibroblasts and regulation of extracellular matrix remodeling through specific metalloprotinases. Together, our data suggest that an εPKC inhibitor, such as εV1-2, may augment current therapeutic strategy for the treatment of heart failure in humans.

II. βIPKC and βIIPKC Inhibitors

Figure 9:
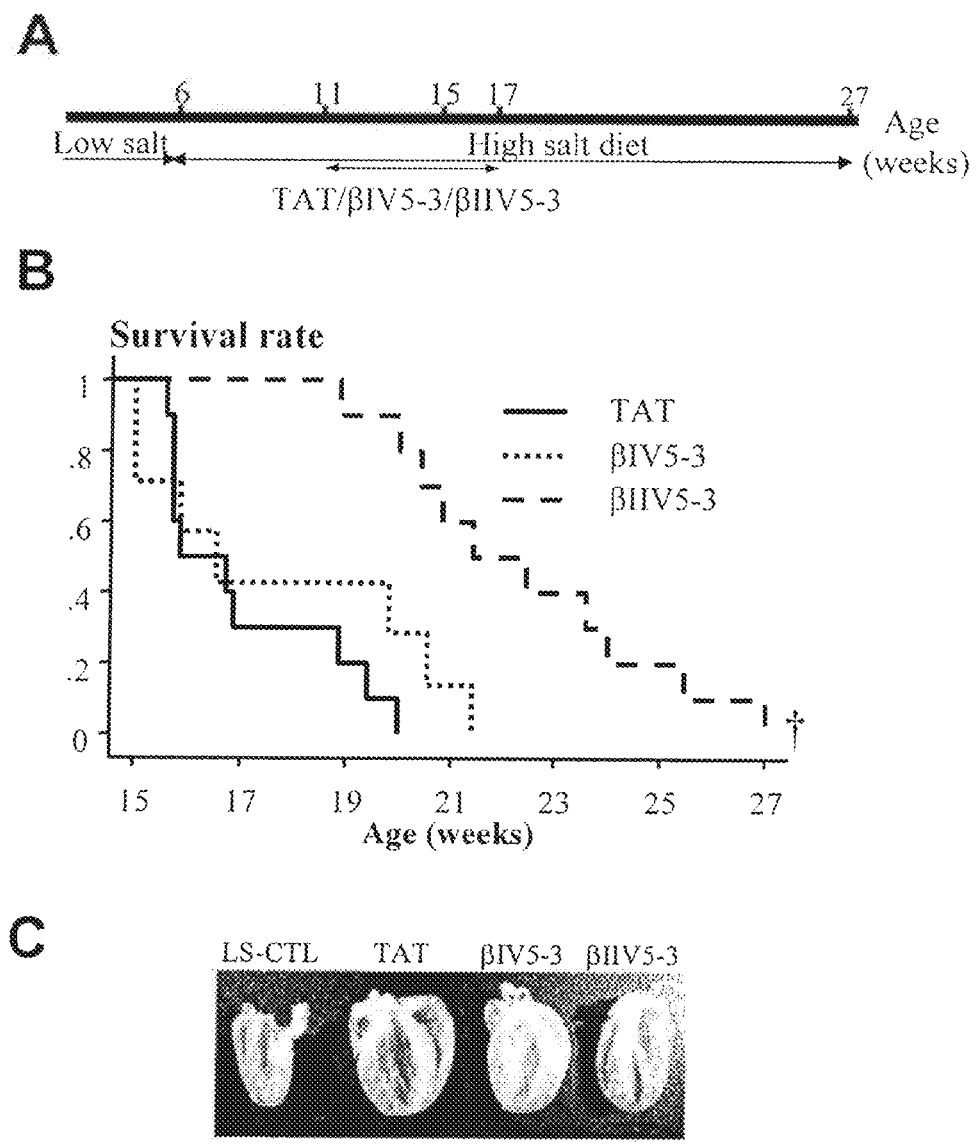
FIG. 9A shows the scheme for the protocol of treatments involving βIPKC and βIIPKC peptides.
FIG. 9B shows the survival rate of rats with hypertension-induced heart failure, and treated for six weeks with either TAT (control), the βIV5-3 peptide, or the βIIV5-3 peptide.
FIGS. 9C-9E show examples of morphological changes (FIG. 9C), changes in echocardiograms (FIG. 9D), and averaged fractional shortening data (FIG. 9E), from each rat group at the age of 11 and 17 weeks.
FIG. 9F shows left ventricular weight to body weight ratio (LVW/BW) measured in 17-weeks old rats.
FIG. 9G shows the systolic blood pressure measured at the age of 11, 13, 15 and 17 weeks. LS-CTL: n=30, Tat: n=16, βIV5-3: n=7, βIV5-3: n=10. *$P<0.05$ vs. LS-C, \$P<0.05$ vs. HS-C.
Figure 9:
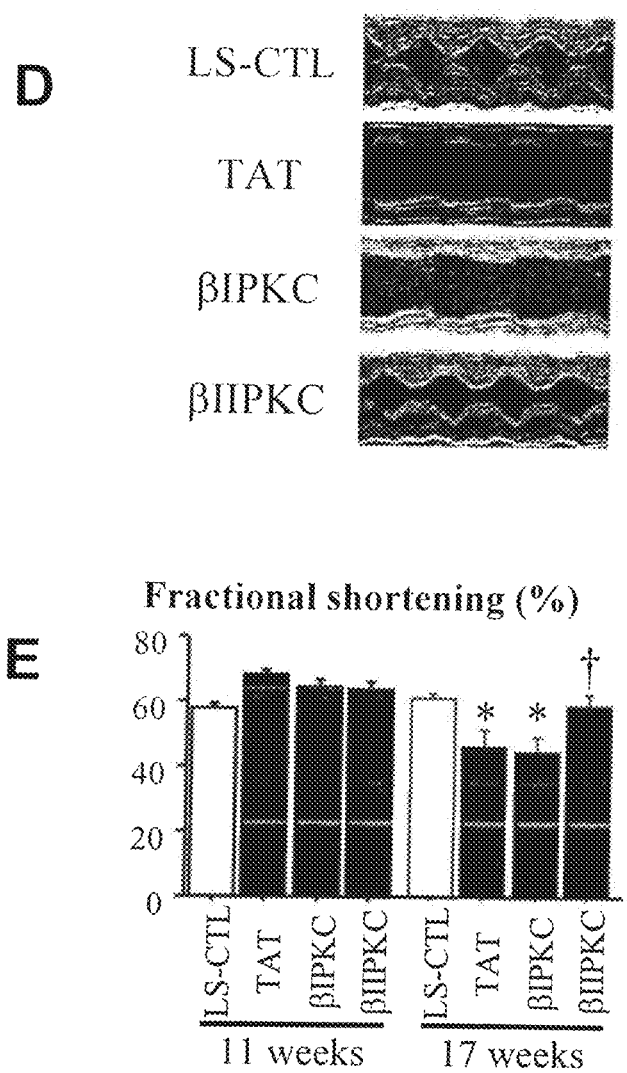
Figure 9:
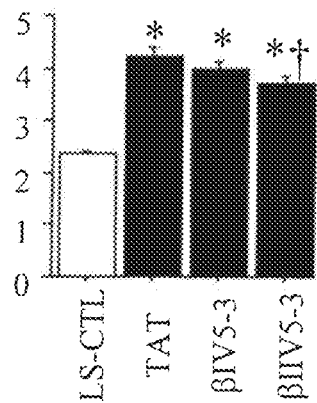
Figure 9:
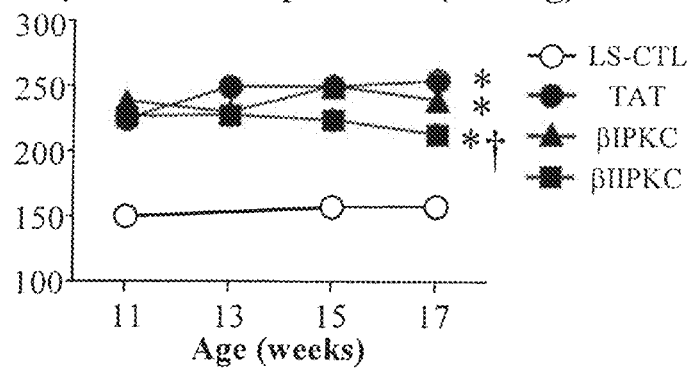
Figure 11:
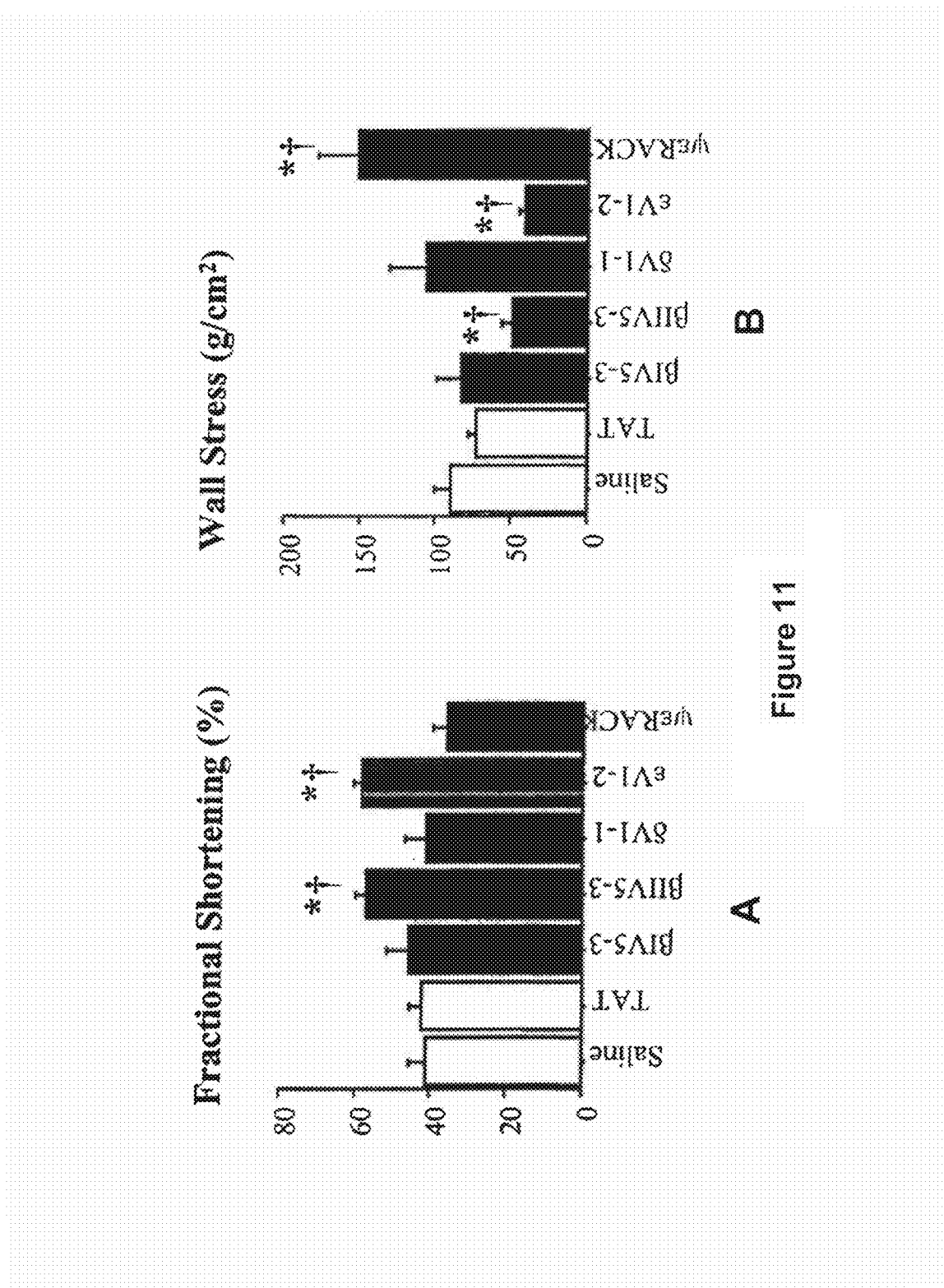
FIGS. 11A and 11B show the percent fractional shortening (FIG. 11A) and the wall stress, in g/cm² (FIG. 11B), in animals treated with saline, TAT peptide, a βIV5-3 PKC peptide inhibitor, a βIIV5-3 peptide inhibitor, δV1-1 peptide inhibitor, εV1-2 PKC peptide inhibitor, ΨεRACK, or an εPKC activator.

In another aspect, a method of inhibiting progression of heart failure by administering a peptide from the V5 domain of βIPKC or βIIPKC is provided. Exemplary peptides are the βIV5-3 peptide and the βIIV5-3 peptide, respectively. As above the peptide is administered to enhance survival of patients experiencing or at risk of heart failure due to chronic hypertension. Data from studies conducted in support of this aspect are presented in FIGS. 9-11.

FIG. 9A shows the scheme for the protocol of treatments involving exemplary βIPKC and βIIPKC peptides, which is similar to that used for treatments involving the εPKC peptides (above). The survival rates of rats with hypertension-induced heart failure, and treated for six weeks with either TAT (control), the βIV5-3 peptide, or the βIIV5-3 peptide is shown in the graph in FIG. 9B. Treatment with the βIV5-3 peptide inhibitor or the βIIV5-3 peptide inhibitor prolonged survival compared to treatment with the TAT control peptide. However, treatment with the βIIV5-3 peptide inhibitor prolonged survival significantly longer than treatment with the βIV5-3 peptide inhibitor.

FIGS. 9C-9E show examples of morphological changes (FIG. 9C), changes in echocardiograms (FIG. 9D), and averaged fractional shortening data (FIG. 9E), from each rat group at the age of 11 and 17 weeks. Treatment with the βIIV5-3 peptide significantly reduced fractional shortening at 17 weeks. Treatment with the βIV5-3 peptide inhibitor or TAT produced similar results. The left ventricular weight to body weight ratio (LVW/BW) measured in 17-weeks old rats was also reduced in βIIV5-3 peptide inhibitor-treated animals (FIG. 9F).

FIG. 9G shows the systolic blood pressure measured at the age of 11, 13, 15 and 17 weeks. *$P<0.05$ vs. LS-C, †$P<0.05$ vs. HS-C. The blood pressure in the βIIV5-3 peptide-treated animals was less than in the TAT or βIV5-3 peptide-treated animals.

FIGS. 10A and 10B show the survival rate from heart failure in rodents as a function of age (FIG. 10A) and blood pressure (FIG. 10B) in animals treated with saline, TAT peptide, a βIV5-3 PKC peptide inhibitor, a βIIV5-3 peptide inhibitor, δV1-1 peptide inhibitor, εV1-2 PKC peptide inhibitor, ΨεRACK, an εPKC activator, or the angiotensin II receptor blocker. FIGS. 11A-11B show the percent fractional shortening (FIG. 11A) and the wall stress, in g/cm², (FIG. 11B), in animals treated with saline, TAT peptide, a βIV5-3 PKC peptide inhibitor, a βIIV5-3 peptide inhibitor, δV1-1 peptide inhibitor, εV1-2 PKC peptide inhibitor, ΨεRACK, or an εPKC activator.

The results using the βIV5-3 and βIIV5-3 peptide inhibitors show that the βIIV5-3 peptide, and to a lesser extent the βIV5-3 peptide, prolongs survival, decreases fractional shortening, and reduces wall stress in hypertensive rats, likely in a manner similar to the εPKC inhibitor εV1-2.

III. Methods for Slowing or Inhibiting the Progression of Heart Failure

The data described herein show that εPKC inhibitors, βIIPKC inhibitors, and, to a lesser extent, βIPKC inhibitors, are effecting in slowing or inhibiting the progression of heart failure in a patients suffering from chronic hypertension. As used here, slowing or inhibiting the progression of heart failure means prolonging survival, reducing fractional shortening, reducing left ventricular weight to body weight ratio, reducing fibrosis, causing the EKG/ECG of a subject to more closely resemble that of a healthy animal (e.g., an animal not suffering from hypertension), and/or combinations thereof.

The εV1-2 PKC peptide inhibitor, βIV5-3 PKC peptide inhibitor, and/or βIIV5-3 peptide inhibitor may include natural amino acids, such as the L-amino acids or non-natural amino acids, such as D-amino acids. The amino acids in the peptide may be linked by peptide bonds or, in modified peptides described herein, by non-peptide bonds.

A wide variety of modifications to the amide bonds which link amino acids may be made and are known in the art. Such modifications are discussed in general reviews, including in Freidinger, R. M. "Design and Synthesis of Novel Bioactive Peptides and Peptidomimetics" *J. Med. Chem.* 46:5553 (2003), and Ripka, A. S., Rich, D. H. "Peptidomimetic Design" *Curr. Opin. Chem. Biol.* 2:441 (1998). These modifications are designed to improve the properties of the peptide by increasing the potency of the peptide or by increasing the half-life of the peptide.

The potency of the peptide may be increased by restricting the conformational flexibility of the peptide. This may be achieved by, for example, including the placement of additional alkyl groups on the nitrogen or alpha-carbon of the amide bond, such as the peptoid strategy of Zuckerman et al, and the alpha modifications of, for example Goodman, M. et. al. [*Pure Appl. Chem.* 68:1303 (1996)]. The amide nitrogen and alpha carbon may be linked together to provide additional constraint [Scott et al, *Org. Letts.* 6:1629-1632 (2004)].

The half-life of the peptide may be increased by introducing non-degradable moieties to the peptide chain. This may be achieved by, for example, replacement of the amide bond by a urea residue [Patil et al, *J. Org. Chem.* 68:7274-7280 (2003)] or an aza-peptide link [Zega and Urleb, *Acta Chim. Slov.* 49:649-662 (2002)]. Other examples of non-degradable moieties that may be introduced to the peptide chain include introduction of an additional carbon ["beta peptides", Gellman, S. H. *Acc. Chem. Res.* 31:173 (1998)] or ethene unit [Hagihara et al, *J. Am. Chem. Soc.* 114:6568 (1992)] to the chain, or the use of hydroxyethylene moieties [Patani, G. A., Lavoie, E. J. *Chem. Rev.* 96:3147-3176 (1996)] and are also well known in the art. Additionally, one or more amino acids may be replaced by an isosteric moiety such as, for example, the pyrrolinones of Hirschmann et al [*J. Am. Chem. Soc.* 122:11037 (2000)], or tetrahydropyrans [Kulesza, A. et al., *Org. Letts.* 5:1163 (2003)].

Although the peptides are described primarily with reference to amino acid sequences from *Rattus norvegicus*, it is understood that the peptides are not limited to the specific amino acid sequences set forth herein. Skilled artisans will recognize that, through the process of mutation and/or evolution, polypeptides of different lengths and having different constituents, e.g., with amino acid insertions, substitutions, deletions, and the like, may arise that are related to, or sufficiently similar to, a sequence set forth herein by virtue of amino acid sequence homology and advantageous functionality as described herein.

The peptide inhibitors described herein also encompass amino acid sequences similar to the amino acid sequences set forth herein that have at least about 50% identity thereto and function to decrease the extent of occlusion in the lumen of a mammalian blood vessel and/or decrease endothelial cell swelling in a mammalian blood vessel, both as described herein. Preferably, the amino acid sequences of the peptide inhibitors encompassed in the invention have at least about 60% identity, further at least about 70% identity, preferably at least about 80% identity, more preferably at least about 90% identity, and further preferably at least about 95% identity, to the amino acid sequences shown herein. Percent identity may be determined, for example, by comparing sequence information using the advanced BLAST computer program, including version 2.2.9, available from the National Institutes of Health. The BLAST program is based on the alignment method of Karlin and Altschul. *Proc. Natl. Acad. Sci. USA* 87:2264-2268 (1990) and as discussed in Altschul, et al., J. Mol. Biol. 215:403-410 (1990); Karlin And Altschul, *Proc. Natl. Acad. Sci. USA* 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the proteins being compared. Default parameters are provided to optimize searches with short query sequences in, for example, blastp with the program. The program also allows use of an SEG filter to mask-off segments of the query sequences as determined by the SEG program of Wootton and Federhen, *Computers and Chemistry* 17:149-163 (1993).

Conservative amino acid substitutions may be made in the amino acid sequences to obtain derivatives of the peptides that may advantageously be utilized in the present invention. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, aspartic acid, glutamic acid and their amides, are also considered interchangeable herein.

Furthermore, in other embodiments, the cell permeable carrier protein or peptide that may increase cellular uptake of the peptide inhibitor may be, for example, a *Drosophila* Antennapedia homeodomain-derived sequence (CRQIKIW-FQNRRMKWKK), and may be attached (i.e., conjugated) to the εPKC, βIPKC, or βII PKC inhibitor by cross-linking via an N-terminal Cys-Cys bond as discussed in Theodore, L., et al. *J. Neurosci.* 15:7158-7167 (1995); Johnson, J. A., et al. *Circ. Res* 79:1086 (1996). In some embodiments, peptide inhibitors are conjugated to cell permeable carrier peptides between cysteine residues on the amino or carboxy-termini of the peptides. Such cysteine residues may be part of the naturally-occurring peptide sequence or may be added to the naturally-occurring peptide sequence.

Alternatively, the inhibitor may be modified by a Transactivating Regulatory Protein (Tat)-derived transport polypeptide (such as from amino acids 47-57 of Tat (YGRKKRRQRRR) from the Human Immunodeficiency Virus, Type 1, as described in Vives, et al., *J. Biol. Chem.*, 272:16010-16017 (1997), U.S. Pat. No. 5,804,604 and Genbank Accession No. AAT48070; or with polyarginine as described in Mitchell, et al. *J. Peptide Res.* 56:318-325 (2000) and Rothbard, et al., *Nature Med.* 6:1253-1257 (2000). Such TAT derived cell permeable carrier peptides may be conjugated to peptide inhibitors between cysteine residues, as described immediately above.

Peptides having both inhibitor sequences and cell permeable carrier peptide sequences, with or without additional cysteine residues, may also be synthesized using standard methods, e.g., to produce a single peptide having both inhibitor peptide and cell permeable carrier peptide sequences.

The inhibitors may be modified by other methods known to the skilled artisan in order to increase the cellular uptake of the inhibitors.

The inhibitors may be advantageously administered in various forms. For example, the inhibitors may be administered in tablet form for sublingual administration, in a solution or emulsion. The inhibitors may also be mixed with a pharmaceutically-acceptable carrier or vehicle. The vehicle may be a liquid, suitable, for example, for parenteral administration, including water, saline or other aqueous solution, or may be an oil or aerosol. The carrier may be selected for intravenous or intraarterial administration, and may include a sterile aqueous or non-aqueous solution that may include preservatives, bacteriostats, buffers and antioxidants known to the art. In the aerosol form, the inhibitor may be used as a powder, with properties including particle size, morphology and surface energy known to the art for optimal dispersability. In tablet form, a solid carrier may include, for example, lactose, starch, carboxymethyl cellulose, dextrin, calcium phosphate, calcium carbonate, synthetic or natural calcium allocate, magnesium oxide, dry aluminum hydroxide, magnesium stearate, sodium bicarbonate, dry yeast or a combination thereof. The tablet preferably includes one or more agents which aid in oral dissolution. The inhibitors may also be administered in forms in which other similar drugs known in the art are administered.

The inhibitors may be administered to a patient by a variety of routes. For example, the inhibitors may be administered parenterally, including intraperitoneally, intravenously, intraarterially, subcutaneously, or intramuscularly. The inhibitors may also be administered via a mucosal surface, including rectally, and intravaginally; intranasally, including by inhalation; sublingually; intraocularly and transdermally. Combinations of these routes of administration are also envisioned. A preferred mode of administration is by infusion or reperfusion through an artery, or an artery that is connected to such an occluded or partially-occluded artery. By "partially-occluded artery" it is meant herein an artery in which blood flow is reduced after an ischemic attack or other hypoxic event affecting the heart blood vessels when compared to blood flow prior to such event or attack.

In certain embodiments, the inhibitors described herein may be co-administered in a composition with a second therapeutic agent.

In this manner, one skilled in the art will recognize that εPKC, βI, PKC, and BIIPKC, individually, in combination, or combined with a second therapeutic agent, may be used to prepare a medicament for the slowing or inhibiting the progression of heart failure in a patients suffering from chronic hypertension.

Further aspects and embodiments will be apparent to the skilled artisan in view of the present teachings. The foregoing description and the following examples are not intended to be limiting.

EXAMPLES

Figure 1:
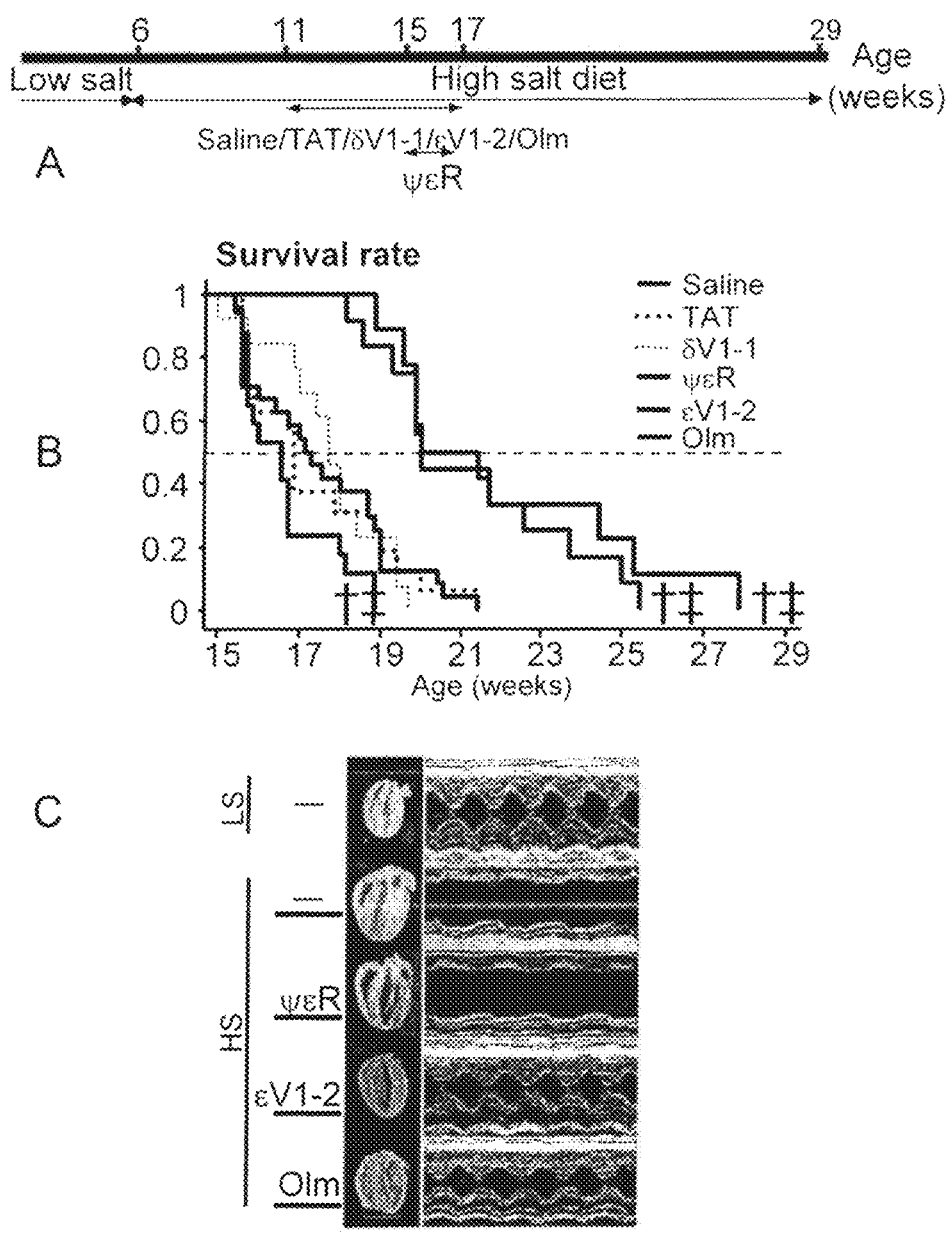
FIG. 1A shows the scheme for the protocol of treatments involving εPKC peptides.
FIG. 1B shows the survival rate of rats with hypertension-induced heart failure, and treated for six weeks with either saline (HS-C, n=12), the εPKC activator, $TAT_{47-57}$-ΨεRACK (ΨεR, n=17), the εPKC inhibitor, $TAT_{47-57}$-εV1-2 (εV1-2, n=10), δV1-1 (n=13), or angiotensin II receptor blocker, olmesartan (Olm, n=12).
FIGS. 1C and 1D show examples of morphological changes (FIG. 1C; images of hearts), changes in echocardiograms (FIG. 1C; traces), and averaged fractional shortening data (FIG. 1D), from each rat group at the age of 11 and 17 weeks.
FIGS. 1E and 1F show lung weight to body weight ratio (LungW/BW.
FIG. 1G shows the systolic blood pressure measured at the age of 11, 13, 15 and 17 weeks (n=6-17 per group). *$P<0.05$ vs. LS-C, †$P<0.05$ vs. HS-C.
Figure 1:
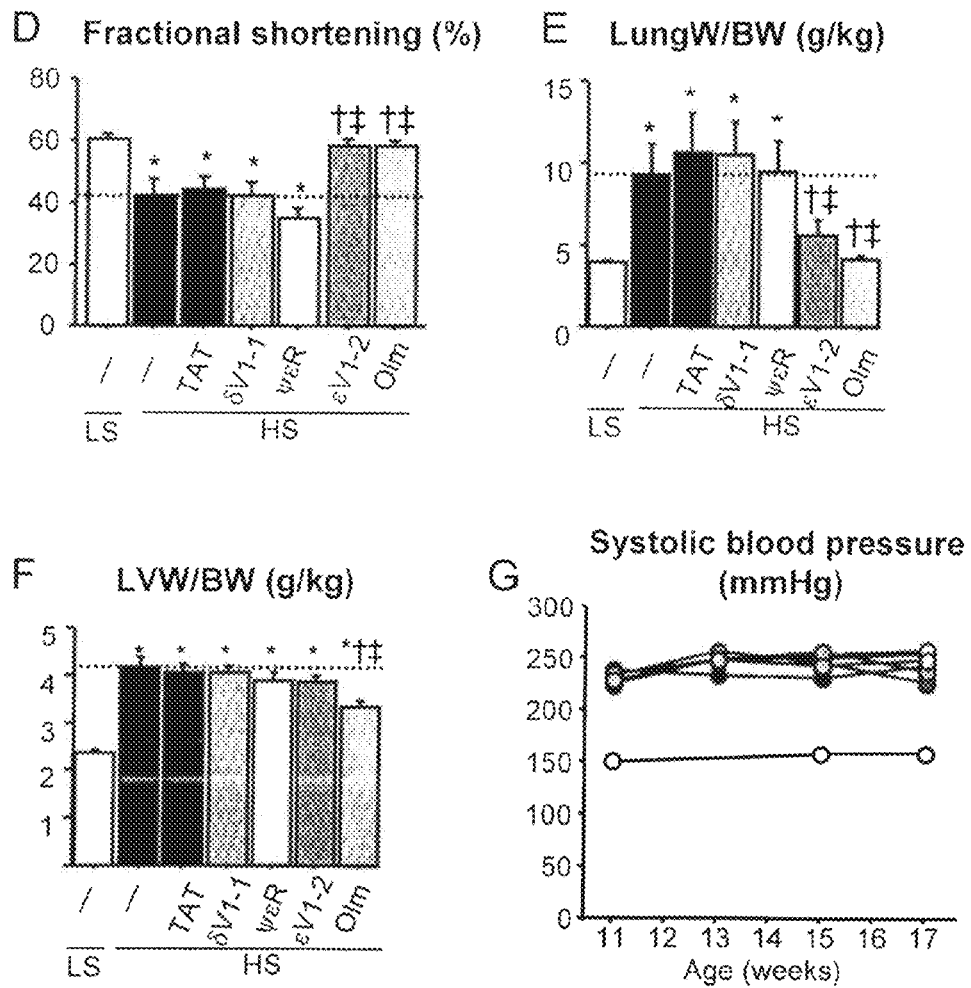

The following examples are illustrative in nature and are in no way intended to be limiting.
1. Peptide Synthesis εV1-2 (εPKC inhibitor, amino acids 14-21; EAVSLKPT; SEQ ID NO: 5) (16, 17) and ΨεRACK (εPKC activator, amino acids 85-92; HDAPIGYD; SEQ ID NO: 6) (18, 19) were synthesized and conjugated them to TAT (carrier peptide, amino acids 47-57; YGRKKRRQRRR; SEQ ID NO: 1) (20) via a cysteine-cysteine S—S bond at their N termini, as previously described (15). Other peptides are described herein and were prepared in a similar manner.
2. Hypertension-Induced Heart Failure Rat Model Animal protocols were approved by the Stanford University Institutional Animal Care and Use Committee. Dahl salt-sensitive rats provide a reliable animal model of hypertension-induced heart failure. When placed on 8% NaCl-containing diet from the age of 6 weeks (HS rats), the rats develop compensatory left ventricular hypertrophy by the age of 11 weeks, and die from heart failure when they reach 16 to 21 weeks (21, 25). Male Dahl salt-sensitive rats were fed with an 8% NaCl-containing diet (Dahl-high-salt) or with a 0.3% NaCl low salt diet (LS-control; n=25) from the age of 6 weeks onward as previously reported (3, 21). Dahl-high-salt rats were treated between the ages of 11 and 17 weeks with the selective εPKC inhibiting peptide, $TAT_{47-57}$-εV1-2 (εV1-2; n=10, 2.8 μg/kg/day), with $TAT_{47-57}$-εV1-1 (εV1-1; n=14, 2.8 μg/kg/day), or with saline as a control (HS-Control; n=12), using osmotic pumps implanted subcutaneously. A fourth group was treated with angiotensin II receptor type 1 blocker, olmesartan (ARB; n=12, 3 mg/kg/day in 0.5% carboxymethylcellulose) delivered by daily gavage for the same period. A fifth group was treated from 15 to 17 weeks of age with the selective εPKC activating peptide, $TAT_{47-57}$-Ψε-RACK (ΨεRACK; n=17, 2.8 μg/kg/day) using an osmotic pump implanted subcutaneously (FIG. 1).

The osmotic pumps were replaced every two weeks, but were discontinued after the age of 17 weeks because half of the HS-control rats died by that age. Additional groups were treated with εV1-2 (using the Alzet pump) together with ARB (n=12) or with ARB alone (n=13) from 11 to 19 weeks of age (FIG. 6). Survival rate, fractional shortening and blood pressure were evaluated in these groups. Systolic blood pressure was measured by the tail-cuff method (BP-2000 Blood Pressure Analysis System, Visitech Systems, Inc), and fractional shortening was measured by transthoracic echocardiography (Vivid 7, GE). Additional control Dahl-high-salt rats were treated with $TAT_{47-57}$ carrier peptide between 11 to 17 weeks or between 15 to 17 weeks, with vehicle for ARB (0.5% carboxymethylcellulose) or were left untreated and evaluated for survival rate, cardiac function and blood pressure.

There were no differences among these control-treated groups in these parameters (data not shown). Blood was withdrawn from 17-week-old rats and serum troponin T levels were determined by the Stanford Clinical Lab (n=8-15 for each group). About 5% of the hypertensive animals developed sterile seroma around the pump, which increased pump mobility under the skin; therefore these animals were euthanized. There were no statistical differences among groups in the incidence of seroma.

3. Histological Analysis

For morphometric analysis, left ventricle (LV) specimens from 17-week-old rats (n=4 for each group) were fixed with 10% buffered formalin and embedded in paraffin. Several sections were prepared from each specimen and stained with either hematoxylin and eosin (H&E) for assessment of inflammation and proliferation of vascular cells, or with Masson's trichrome stain to assess the area of cardiac fibrosis using a point-counting method (22, 23).

4. Western Blot Analysis

The expression and translocation of $\epsilon$ and $\delta$PKC in LV tissues from 17-week-old rats were determined by western blot analysis as previously reported (3) (n=6 for each group). LV samples to be used for PKC expression and for PKC translocation were prepared separately. The soluble fractions of total proteins were separated by a 1 hour centrifugation at 100,000 g after homogenization of the LV myocardium (0.3 g) in sample buffer. Particulate fractions were homogenized in sample buffer containing 1.0% Triton X-100 and centrifuged at 100,000 g for 1 hour. Whole tissue lysates were obtained by homogenization of LV myocardium (0.3 g) in sample buffer with 1.0% Triton X-100. Protein concentration was determined by the Bradford method. All samples (20 µg) were electrophoresed on an 8% SDS-polyacrylamide gel and the proteins were transferred to a nitrocellulose membrane. All membranes were stained with Ponceau S to confirm equal transfer efficiency. Adequate background blocking was accomplished by incubating the nitrocellulose membranes with 5% nonfat dry milk in Tris-buffered saline. The immunoblotting was performed using anti-$\epsilon$ and $\delta$PKC rabbit polyclonal antibodies (Santa Cruz Biotechnology, Santa Cruz, Calif.) diluted 1:1000 followed by goat anti-rabbit IgG antibodies diluted 1:2000. PKC was visualized by the enhanced chemiluminescence method and levels in each sample were shown as the ratio to that in LS-control group.

5. Real-Time PCR

Two µg of total RNA extracted from the LV tissues of each 7-week-old rat (n=6 for each group) were converted to first-strand cDNA by reverse transcription using High Capacity cDNA Archive kit (Applied Biosystems). Real-time PCR was performed with commercially available TaqMan® assays and TaqMan® Universal Master Mix (see supplementary methods). After 2 minutes at 50° C. and 10 minutes at 95° C., 40 cycles of amplification were performed, each at 95° C. for 15 seconds and 60° C. for 1 minute, using the 7900HT Sequence Detection System (Applied Biosystems). Data was collected using SDS 2.1 software (Applied Biosystems). Each PCR was set up in quadruplicate. The fluorescence signals were normalized to the ubiquitously expressed housekeeping gene, β-actin. Fold-changes of mRNA expression of each group compared to the LS-control were determined by comparing cycle threshold values (24). Statistical analysis was assessed by 1-way factorial ANOVA with Fisher's test. A value of P<0.05 was considered significant.

6. In-Gel Zymography

MMP-2 activity was measured by in-gel zymography as described previously (31). Briefly, LV tissues were homogenized in ice-cold lysis buffer (10 mM HEPES-NaOH, pH7.4, 0.9% NaCl, 1 mM EDTA, 1% Triton X-100, phosphatase inhibitor cocktail from SIGMA-Aldrich). The lysates were centrifuged for 15 minutes at 15,000 rpm 4° C. and the supernatants were collected on ice. 10 µg of protein was loaded and resolved by SDS-polyacrylamide gel containing 1 mg/mL gelatin (Sigma-Aldrich). Gels were subjected to two 30 minute washes in 2.5% Triton X-100, followed by 15 minute incubation in developing buffer (50 mM Tris-HCl pH 8.0, 5.0 mM $CaCl_2$, 0.02% $NaN_3$). Gels were then incubated in new developing buffer for 24 to 48 hours at 37° C., stained with Coomassie Blue R-250 and destained in 40% ethanol containing 10% acetic acid. The clear or unstained bands corresponding to digestion of gelatin by MMP-2 were quantified using ImageJ 1.35s software (http://rsb.info.nih.gov/ij/).

7. Collagen Secretion from Primary Cardiac Cultured Fibroblasts

We isolated neonatal rat fibroblasts as previously described (50). Briefly, neonatal cardiac non-myocytes were prepared from 1-2 day-old Sprague-Dawley rats. Hearts were harvested, ventricles were dissected from the atria, cycles of digestion and centrifugation were performed. The obtained cell suspension was plated on four 100 mm plates at 37° C. for 1 hour, during which time the non-myocytes (mainly fibroblasts) adhere to the plate while the myocytes remain in suspension. The fibroblasts were cultured in MEM containing 10% FBS, 80 µM ascorbic acid, 50 ng/mL vit B12, 20 µg/mL transferrin, and 10 µg/mL insulin. Confluent fibroblasts were serum-starved for 48 hours before treatment. $\epsilon$V1-2 or $\Psi\epsilon$RACK (1 µM) was administered 15 minutes before a single TGFβ1 treatment (R&D systems, 10 ng/mL) and every 4 hours thereafter. Cells from passages 2-4 were used for all experiments. Secreted collagen in medium was measured using the Sircol soluble collagen assay kit (Biocolor, UK) as previously described (51).

8. Statistics

Data are expressed as mean±SEM. Statistical analysis was assessed by 1-way factorial ANOVA with Fisher's test, 2-way repeated ANOVA or Student's t-test when appropriate. Survival was analyzed by the standard Kaplan-Meier analysis with log-rank test. A value of P<0.05 was considered significant.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method for slowing or inhibiting the progression of heart failure in a mammalian subject suffering from chronic hypertension, comprising: administering to the subject a therapeutically effective amount of a βII Protein Kinase C (βIIPKC) peptide inhibitor from the V5 domain of βIIPKC, wherein the βIIPKC peptide inhibitor specifically inhibits βIIPKC, and wherein the βIIPKC peptide inhibitor is a polypeptide having at least 80% sequence identity to the polypeptide of SEQ ID NO:3.

2. The method of claim 1, wherein the βIIPKC peptide inhibitor consists of βIIV5-3 (SEQ ID NO:3).

3. The method of claim 1, wherein the βIIPKC peptide inhibitor is conjugated to a peptide that increases cellular uptake of the peptide inhibitor.

4. The method of claim 3, wherein the peptide that increases cellular uptake of the peptide inhibitor is a TAT peptide comprising the polypeptide of SEQ ID NO:1.

5. The method of claim 4, wherein the TAT peptide consists of the polypeptide of SEQ ID NO:1.

6. The method of claim 1, wherein the βIIPKC peptide inhibitor is administered in combination with olmesartan.

7. The method of claim 1, wherein the mammalian subject is a heart transplant patient.

* * * * *

UNITED STATES PATENT AND TRADEMARK OFFICE
CERTIFICATE OF CORRECTION

PATENT NO. : 8,426,364 B2
APPLICATION NO. : 12/774669
DATED : April 23, 2013
INVENTOR(S) : Daria Mochly-Rosen and Koichi K. Inagaki It is certified that error appears in the above-identified patent and that said Letters Patent is hereby corrected as shown below:

In the Specifications

Column 1, line 18, should read

This invention was made with government support under contract ~~the support of National Institute of Health Grant number~~ HL-076675 awarded by the National Institutes of Health. ~~Accordingly the United States government~~ The Government has certain rights in this invention.

Signed and Sealed this
Twenty-first Day of May, 2013

Teresa Stanek Rea
*Acting Director of the United States Patent and Trademark Office*